(12) United States Patent
Chevalier

(10) Patent No.: US 12,419,626 B2
(45) Date of Patent: *Sep. 23, 2025

(54) BONE DISTRACTION DEVICES AND METHODS OF USING SAME

(71) Applicant: NuVasive, Inc., San Diego, CA (US)

(72) Inventor: Eric Chevalier, Arras (FR)

(73) Assignee: NuVasive, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/747,777

(22) Filed: Jun. 19, 2024

(65) Prior Publication Data
US 2024/0341743 A1    Oct. 17, 2024

Related U.S. Application Data

(63) Continuation of application No. 17/294,418, filed as application No. PCT/US2019/061893 on Nov. 16, 2019, now Pat. No. 12,029,407.

(60) Provisional application No. 62/768,814, filed on Nov. 16, 2018, provisional application No. 62/768,819, filed on Nov. 16, 2018.

(51) Int. Cl.
*A61B 17/02* (2006.01)
*A61B 17/00* (2006.01)

(52) U.S. Cl.
CPC .. *A61B 17/025* (2013.01); *A61B 2017/00075* (2013.01); *A61B 2017/00221* (2013.01); *A61B 2017/00407* (2013.01); *A61B 2017/00867* (2013.01); *A61B 2503/06* (2013.01); *A61B 2562/0204* (2013.01)

(58) Field of Classification Search
CPC ........ A61B 17/025; A61B 2017/00075; A61B 2017/00221; A61B 2017/00407; A61B 2017/00867; A61B 2503/06; A61B 2562/0204
USPC ..................... 606/70–71, 105, 280–299, 279
See application file for complete search history.

(56) References Cited

U.S. PATENT DOCUMENTS

| | | | | |
|---|---|---|---|---|
| 3,547,114 A * | 12/1970 | Haboush | ............ | A61B 17/8009 606/105 |
| 3,604,414 A * | 9/1971 | Borges | ............... | A61B 17/8019 606/105 |
| 5,672,177 A * | 9/1997 | Seldin | ................ | A61B 17/8009 606/105 |
| 5,827,286 A * | 10/1998 | Incavo | ................ | A61B 17/8009 606/282 |
| 6,277,124 B1 * | 8/2001 | Haag | .................... | A61B 17/663 606/57 |
| 6,852,113 B2 * | 2/2005 | Nathanson | ......... | A61B 17/8095 606/71 |
| 7,182,785 B2 * | 2/2007 | Elsalanty | ............ | A61B 17/8071 606/915 |
| 7,635,364 B2 * | 12/2009 | Barrall | ............... | A61B 17/8047 606/70 |
| 2009/0131943 A1 * | 5/2009 | Fischer | ................ | A61B 17/025 606/90 |
| 2010/0076444 A1 * | 3/2010 | Staehler | ............. | A61B 17/8009 606/90 |
| 2010/0198221 A1 * | 8/2010 | Hearn | ................ | A61B 17/8009 606/71 |
| 2013/0138017 A1 * | 5/2013 | Jundt | ..................... | A61B 17/66 601/2 |

* cited by examiner

*Primary Examiner* — Jessica Weiss

(57) ABSTRACT

The present disclosure provides implantable bone distraction devices and methods of using same to elongate a bone.

19 Claims, 19 Drawing Sheets

BONE DISTRACTION DEVICES AND METHODS OF USING SAME

PRIORITY CLAIM

This application is a continuation of U.S. patent application Ser. No. 17/294,418, filed May 17, 2021, which is a national stage entry of PCT Patent Application Serial No. PCT/US19/61893, filed Nov. 16, 2019, which claims priority to U.S. Provisional Patent Application Ser. No. 62/768,814, filed Nov. 16, 2018, and U.S. Provisional Patent Application Ser. No. 62/768,819, filed Nov. 16, 2018, the entire contents of each of which are incorporated herein and relied upon.

FIELD OF DISCLOSURE

The present disclosure provides implantable bone distraction devices and methods of using same to elongate a bone.

BACKGROUND

Distraction osteogenesis procedures cause two segments of bone to be gradually distracted apart. New bone tissue forms in the gap between the two bone segments, thus elongating the overall bone. Distraction osteogenesis can be performed on a bone that is previously fractured or on bone that is purposely fractured surgically by corticotomy or osteotomy.

Existing bone lengthening techniques generally require external fixation through complex and bulky scaffold arrays that penetrate through the patient's skin at multiple locations. Complications with known methods for lengthening bones are frequent; one study by B. Vargas Barreto et al. (2007) logged 90 complications in just 97 bone lengthening processes performed on 57 unique patients—an average of more than one complication per lengthened bone.

Intramedullary nails associated with a remotely-controlled implanted motor can sometimes be used instead of external scaffolding. However, such the motorized intramedullary nails generally require an implanted subcutaneous antenna, thus complicating the surgical procedure and making it more invasive. These devices are therefore designed to lengthen bone segments in a controlled manner, but due to their complexity, may not be manufacturable as an affordable product.

Others have utilized intramedullary distractor containing an implanted magnet, which allows the distraction to be driven electromagnetically by an external stator e.g., a large electromagnet) that for example, causes the implanted magnet to rotate a lead screw that extends a distraction shaft.

Common techniques for lengthening bones are generally limited to large bones of the anatomy, such as tibias and fibias. Lengthening of smaller bones, such as bones of children, or metacarpal or metatarsal bones of children or adults, is significantly more difficult and risky using existing technologies.

Especially for bones of the extremities, the implantable distractor size requirements, in particular thickness, make very difficult to integrate actuators, such as the above-mentioned technologies, to ensure ample required driving distraction force.

There remains a need for improved distraction technologies and methods that are suitable for small bone indications. The present disclosure describes systems and methods that meet that need.

SUMMARY

The present disclosure provides implantable bone distraction devices and methods of using same to elongate a bone.

In one embodiment, the present disclosure provides a subcutaneous bone distraction device 1 comprising a first block portion 3 including a pair of opposing rails 3a and a pair of opposing ratchet sections 4; and a second block portion 3' that slidably mates with the first block portion 3 and includes a first locking pawl 5 and a push button expansion system 5'-6-7-8-8' for incrementally and slidably advancing the second block portion 3' along the pair of opposing rails 3a of the first block portion 3.

In another embodiment, the present disclosure provides a method of lengthening a bone in a subject, the method comprising: anchoring a first block portion 3 of a subcutaneous bone distraction device 1 to a first bone section 2; anchoring a second block portion 3' of a subcutaneous bone distraction device 1 to a second bone section 2': actuating a push button expansion system 5'-6-7-8-8' to incrementally and slidably advance the second block portion 3' along a pair of opposing rails 3a of the first block portion 3; waiting a length of time; thereafter actuating the push button expansion system 5'-6-7-8-8' to incrementally and slidably advance the second block portion 3' along the pair of opposing rails 3a of the first block portion 3; and repeating the steps of waiting a length of time and thereafter actuating the expansion system until the bone has been lengthened to a desired length.

In one embodiment, the present disclosure provides a bone distraction device (100) comprising: a first block portion (103) including a pair of opposing rails (103a, 103b) and a pair of opposing ratchet sections (104); and a second block portion (103') that slidably mates with the first block portion (103) and includes a first locking pawl (105) and an expansion system (107) for incrementally and slidably advancing the second block portion (103') along the pair of opposing rails (103a, 103b) of the first block portion (103).

In another embodiment, the present disclosure provides a bone distraction device (200) comprising: a first block portion (203) including at least one slot or groove (203a, 203b) parallel to a length of the first block portion (203) and pair of opposing ratchet sections (204) along the length of the first block portion (203); and a second block portion (207'/207") that slidably mates with the first block portion (203) and includes a first locking pawl (205') and an expansion system (207) for incrementally and slidably advancing the second block portion (207'/207") along the at least one slot or groove (203a,203b) of the first block portion (203).

In another embodiment, the present disclosure provides a modular actuator for a bone distraction device, the modular actuator comprising: a first floating element (207') comprising at least one locking pawl (205'): a second floating element (207") comprising at least one locking pawl (205) and separated from the first floating element (207') by a baseline distance: at least one length of shape memory alloy (207a) connected to the first floating element (207') and to the second floating element (207"); and a spring (208) connected to the first floating element (207') and to the second floating element (207"), wherein activation of the at least one length of shape memory alloy (207a) forces the first floating element (207') to come closer to the second floating element (207") by a reduced distance that is smaller than the baseline distance, compressing the spring (208) and wherein the released energy of the spring (208) causes the second floating element (207") to move away the first floating element (207') in order to obtain again the baseline distance for a next cycle.

In another embodiment, the present disclosure provides a method of lengthening a bone in a subject, the method comprising: anchoring a first plate of a bone distraction device to a first bone segment of the subject; anchoring a second plate of the bone distraction device to a second bone segment of the subject; thereafter associating a remotely-actuated expansion system with the first plate and the second plate; remotely actuating the remote-actuated expansion system, after callus bone has formed between the first bone segment and the second bone segment, to force the first plate and the second plate apart relative to each other; thereafter allowing additional callus bone to form between the first bone segment and the second bone segment; and repeating the steps of remotely actuating the remote-actuated expansion system and thereafter allowing additional callus bone to form between the first bone segment and the second bone segment until the bone has been lengthened to a desired extent.

In one embodiment, the present disclosure provides a bone distraction device (2100) comprising: a first block portion (2103) including a pair of opposing rails (2103a, 2103b) and a pair of opposing ratchet sections (2104); and a second block portion (2103') that slidably mates with the first block portion (2103) and includes a first locking pawl (2105) and an expansion system (2107) for incrementally and slidably advancing the second block portion (2103') along the pair of opposing rails (2103a,2103b) of the first block portion (2103). In another embodiment, the present disclosure provides a bone distraction device (2200) comprising: a first block portion (2203) including at least one slot or groove (2203a,2203b) parallel to a length of the first block portion (2203) and pair of opposing ratchet sections (2204) along the length of the first block portion (2203); and a second block portion (2207'/2207") that slidably mates with the first block portion (2203) and includes a first locking pawl (2205') and an expansion system (2207) for incrementally and slidably advancing the second block portion (2207'/2207") along the at least one slot or groove (2203a,2203b) of the first block portion (2203).

In another embodiment, the present disclosure provides a modular actuator for a bone distraction device, the modular actuator comprising: a first floating element (2207') comprising at least one locking pawl (2205'): a second floating element (2207") comprising at least one locking pawl (2205) and separated from the first floating element (2207') by a baseline distance: at least one length of shape memory alloy (2207a) connected to the first floating element (2207') and to the second floating element (2207"); and a spring (2208) connected to the first floating element (2207') and to the second floating element (2207"), wherein activation of the at least one length of shape memory alloy (2207a) forces the first floating element (2207') to come closer to the second floating element (2207") by a reduced distance that is smaller than the baseline distance, compressing the spring (2208) and wherein the released energy of the spring (2208) causes the second floating element (2207") to move away the first floating element (2207') in order to obtain again the baseline distance for a next cycle.

In another embodiment, the present disclosure provides a method of lengthening a bone in a subject, the method comprising: anchoring a first plate of a bone distraction device to a first bone segment of the subject; anchoring a second plate of the bone distraction device to a second bone segment of the subject; thereafter associating a remotely-actuated expansion system with the first plate and the second plate; remotely actuating the remote-actuated expansion system, after callus bone has formed between the first bone segment and the second bone segment, to force the first plate and the second plate apart relative to each other; thereafter allowing additional callus bone to form between the first bone segment and the second bone segment; and repeating the steps of remotely actuating the remote-actuated expansion system and thereafter allowing additional callus bone to form between the first bone segment and the second bone segment until the bone has been lengthened to a desired extent.

These and other embodiments are described in greater detail herein.

DETAILED DESCRIPTION

Referring generally to FIGS. 1-23, the present disclosure provides devices and methods for lengthening a bone of a subject, especially a bone of a child or adolescent or a small bone of an adult such as a bone of a hand or a foot.

1. Subcutaneous Push-Button Bone Distraction Devices

Subcutaneous bone distraction devices 1 consistent with the present disclosure generally comprise a first block portion 3 for anchoring to a first bone segment 2, a second block portion 3' for anchoring to a second bone segment 2', and a push button expansion system (5'-6-7-8-8') that enables the subcutaneous bone distraction devices 1 to expand in a single direction upon input from a user. The first bone segment 2 should be in close enough proximity to the second bone segment 2' that callus bone will grow between the two bone segments. The first block portion 3 and the second block portion 3' interconnect in a manner that allows the subcutaneous bone distraction devices 1 can slidably expand. In some embodiments, the subcutaneous bone distraction device 1 slidably expands, but is configured to prevent the subcutaneous bone distraction device 1 from slidably contracting after anchoring to the first bone segment 2 and to the second bone segment 2'.

Figure 1:
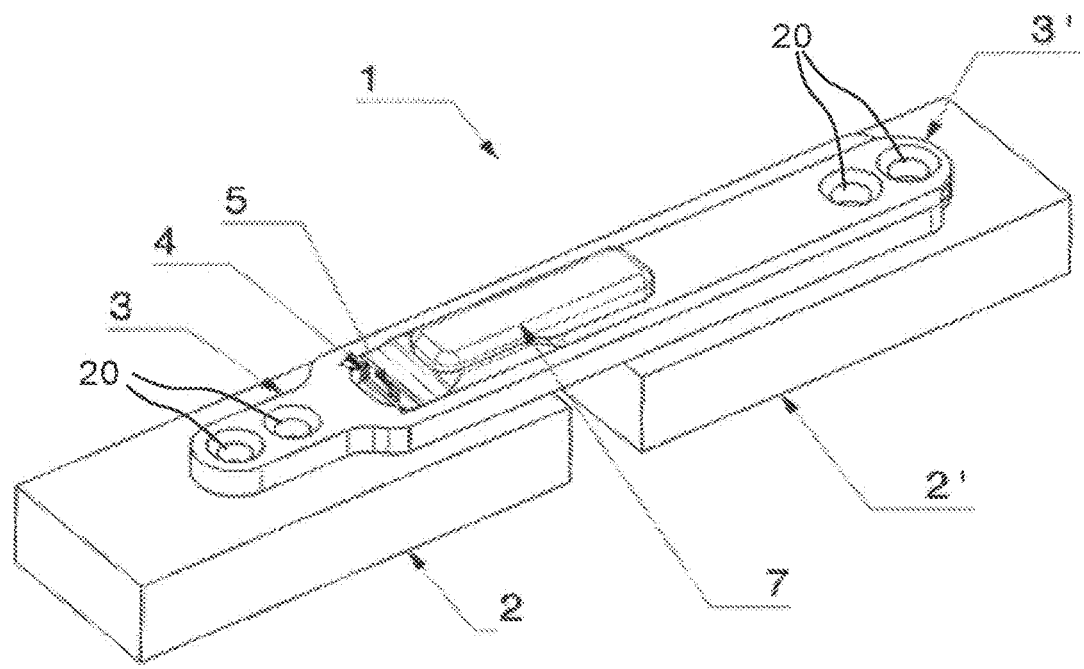
FIG. 1 shows a perspective view of a subcutaneous bone distraction device anchored to two bone segments according to one embodiment of the present disclosure.

Referring now to FIG. 1, a subcutaneous bone distraction device 1 according to the present disclosure comprises a first block portion 3, and a second block portion 3' slidably associated with the first block portion 3.

The first block portion 3 may include one or more anchor holes 20 for securing the first block portion 3 to a first bone segment 2 using any suitable fastener such as a surgical screw (not shown). In some embodiments, the first block portion 3 includes at least two anchor holes 20.

The first block portion 3 may further include a ratchet 4 for enabling incremental expansion of the subcutaneous bone distraction device 1 upon input from a user. In some embodiments, the ratchet includes a plurality of teeth that are spaced at a constant distance to provide even incremental expansion of the subcutaneous bone distraction device 1 with each input by the user. In some embodiments, the spacing between the plurality of teeth is about 0.01 mm to 1 mm, for example about 0.01 mm, about 0.02 mm, about 0.03 mm, about 0.04 mm, about 0.05 mm, about 0.06 mm, about 0.07 mm, about 0.08 mm, about 0.09 mm, about 0.1 mm, about 0.15 mm, about 0.2 mm, about 0.25 mm, about 0.3 mm, about 0.35 mm, about 0.4 mm, about 0.45 mm, about 0.5 mm, about 0.55 mm, about 0.6 mm, about 0.65 mm, about 0.7 mm, about 0.75 mm, about 0.8 mm, about 0.85 mm, about 0.9 mm, about 0.95 mm, about 1 mm. In some embodiments, the spacing between the plurality of teeth is about 0.2 mm.

In other embodiments, the ratchet 4 includes a plurality of teeth spaced at varying distances to enable incremental expansion of the subcutaneous bone distraction device 1 with subsequent inputs by the user. For example and without limitation, in some embodiments the ratchet 4 may include teeth spaced at repeating intervals of about 0.25 mm, 0.25 mm, 0.25 mm, 0.5 mm, 0.25 mm, 0.25 mm, 0.25 mm, 0.5 mm, etc. In such embodiments, the larger interval enables the user to expand the subcutaneous bone distraction device 1 just once before an overnight rest period without being forced to wake before dawn to provide an additional input to expand the subcutaneous bone distraction device 1.

The second block portion 3' includes one or more anchor holes 20 for securing the second block portion 3' to a second bone segment 2' using any suitable fastener such as a surgical screw (not shown). In some embodiments, the first block portion 3 includes at least two anchor holes 20.

The second block portion 3' may additionally include a first locking pawl 5 that engages with the ratchet 4 to provide incremental expansion of the subcutaneous bone distraction device 1 along the length of the first block portion 3. In some embodiments, the first locking pawl comprises a flexible plate that is free to flex in one direction to allow the second block portion 3' to slide in one direction against the first block portion 3, but is not free to flex in the opposite direction, preventing the second block portion 3' from sliding in the opposite direction against the first block portion 3.

The second block portion 3' may additionally include an actuator 7 for receiving input from the user. For example, in the embodiment shown in FIG. 1, the actuator 7 includes a push button that is configured to receive an input force from the user. The actuator 7 may be a component of a push button expansion system (5'-6-7-8-8'), described in more detail below, that converts an input force from the user into lateral expansion of the subcutaneous bone distraction device 1.

In other embodiments, the actuator 7 may be a component of the first block portion 3. In such embodiments, the second block portion 3' may include the ratchet 4, for example on the outside edges of the second block portion 3', or on an inner channel of the second block portion 3'. Activation of the actuator 7 (e.g., pressing on the actuator 7) forces the second block portion 3' away from the first block portion 3 in a stepwise, incremental manner.

Figure 2:
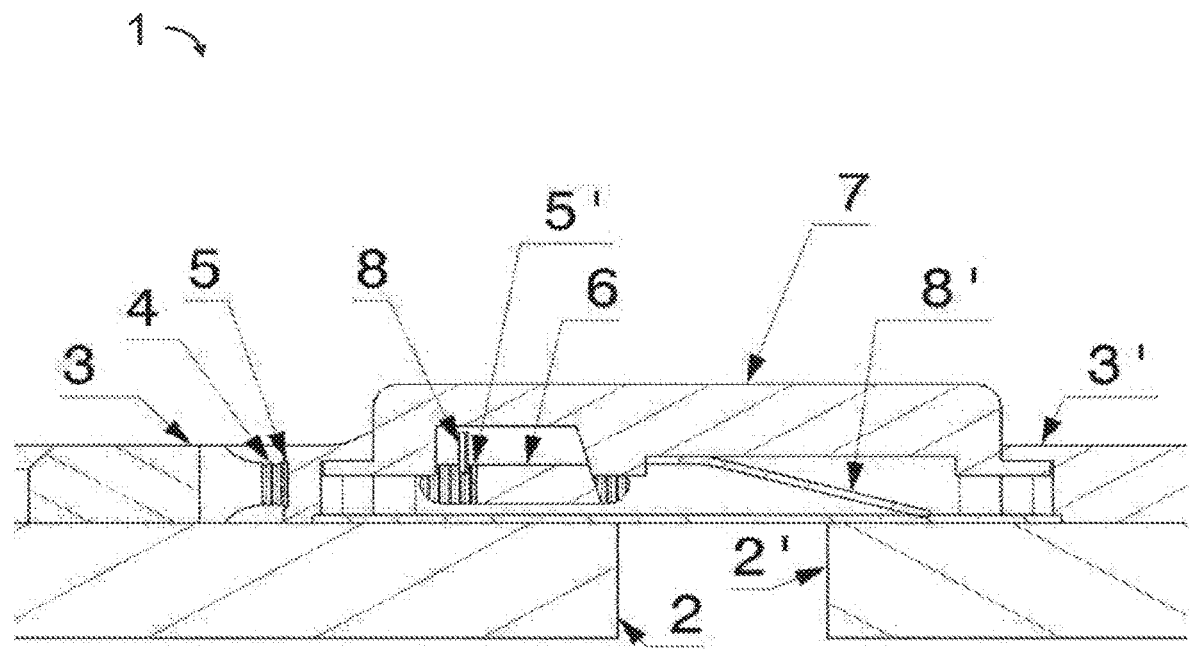
FIG. 2 shows a cross sectional side view of the subcutaneous bone distraction device of FIG. 1 anchored to two bone segments.
Figure 3:
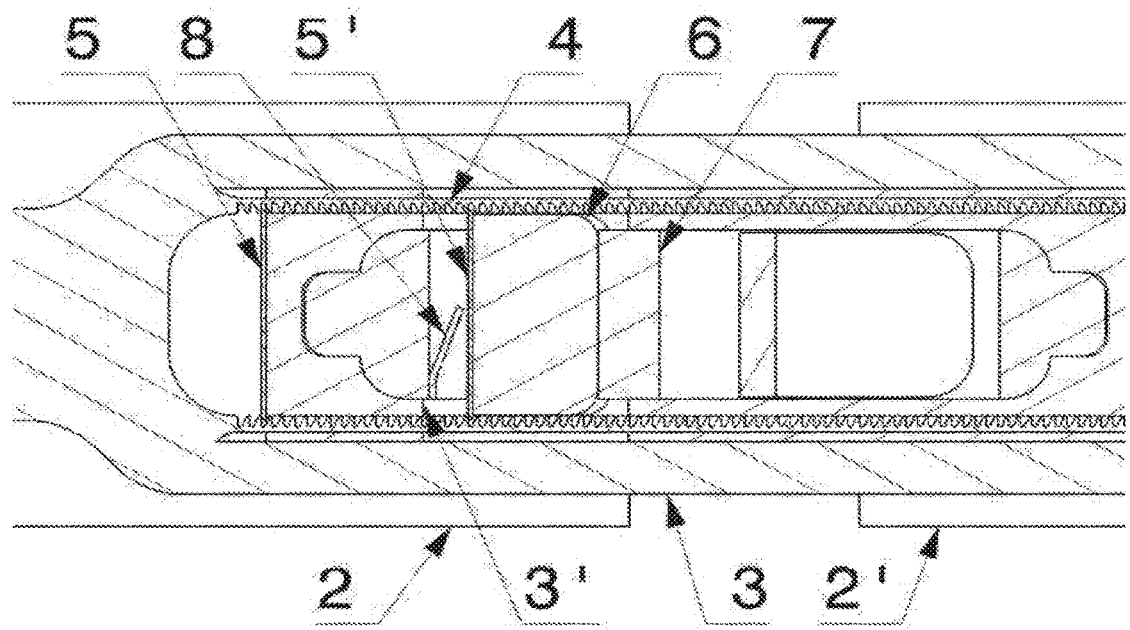
FIG. 3 shows a cross sectional top view of the subcutaneous bone distraction device of FIG. 1 anchored to two bone segments.

One embodiment of the push button expansion system (5'-6-7-8-8') can be seen more clearly in FIGS. 2-3. In this embodiment, the actuator 7 and the first locking pawl 5 are components of the second block portion 3', and the ratchet 4 is a component of the first block portion 3. A floating element 6 is in mechanical communication with the actuator 7. Complementary and overlapping angled surfaces of the actuator 7 and the floating element 6 convert downward force applied to the actuator into lateral force; the floating element is restricted from moving towards the first block portion 3 (i.e., to the left in FIG. 2) by a second locking pawl 5' associated with the face of the floating element opposite the angled surface. The second locking pawl 5' engages with the ratchet 4 to restrict movement of the floating element 6 towards the first block portion 3 (i.e., to the left in FIG. 2). A first energy storage device 8 applies lateral force to the floating element 6 to force the floating element 6 to move away from the first block portion 3 (i.e., to the right in FIG. 2) when the actuator 7 is returned to its original, elevated position by a second energy storage device 8'. In some embodiments, the first energy storage device 8 is a spring, such as a bent tab spring as shown in FIGS. 2-3. In some embodiments, the second energy storage device 8' is a spring, such as a bent leaf spring as shown in FIGS. 2-3.

Figure 4:
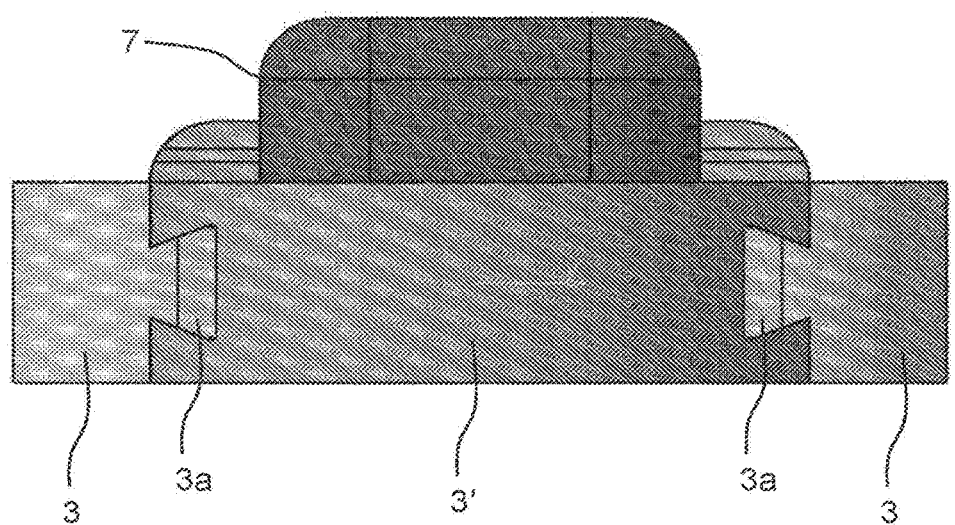
FIG. 4 shows a cross sectional end view of the subcutaneous bone distraction device of FIG. 1.

Referring now to FIG. 4, the second block portion 3' may slidably mate with the first block portion 3 along one or more rails 3a. In some embodiments, such as that shown in FIG. 4, the one or more rails are a component of the first block portion 3'. In such embodiments, the one or more rails 3a may be in line with the ratchet 4, such that the one or more rails 3a serve as a positive stop that limits the expansion of the subcutaneous bone distraction device 1 when the second block portion 3' is advanced until the second locking pawl 5' has reached the end of the ratchet 4 and the beginning of the one or more rails 3a.

In some embodiments, such as that shown in FIG. 4, the one or more rails 3a have a cross sectional shape of a circle, an oval, a square, a rectangle, a pentagon, or a hexagon. In some embodiments, the one or more rails 3a have a trapezoidal cross-sectional shape. Such a shape provides additional stability over rails 3a that have a rectangular or square cross-sectional shape. For example, trapezoidal shaped rails 3a such as those shown in FIG. 4 provide structural stability against undesired separation of the first block portion 3 and the second block portion 3' when the user applies downward force to the actuator 7.

Figure 5A:
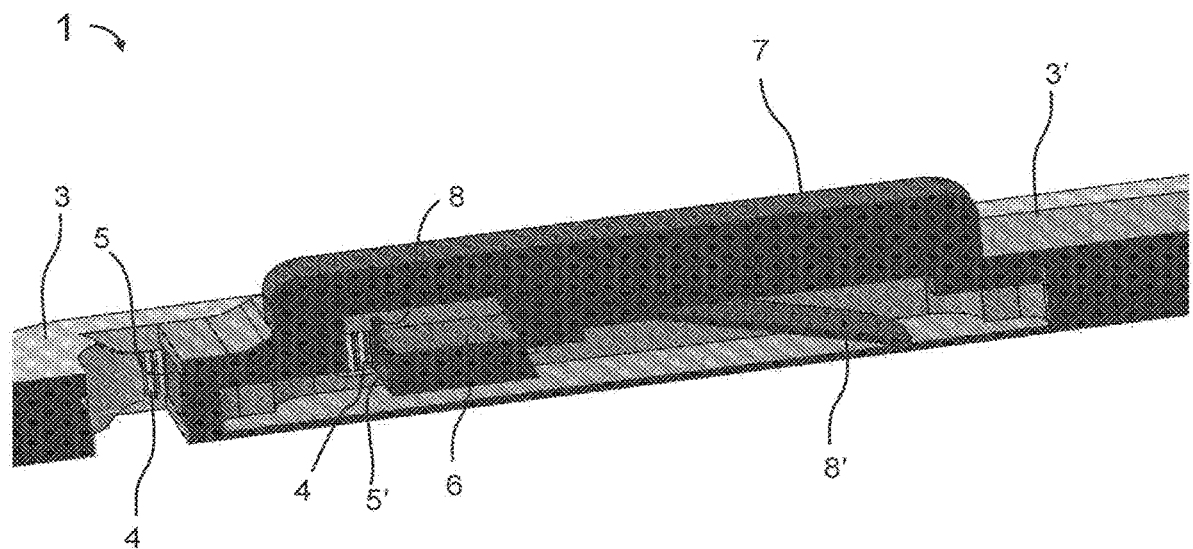
FIG. 5A shows a cutaway side perspective view of the subcutaneous bone distraction device of FIG. 1.
Figure 5B:
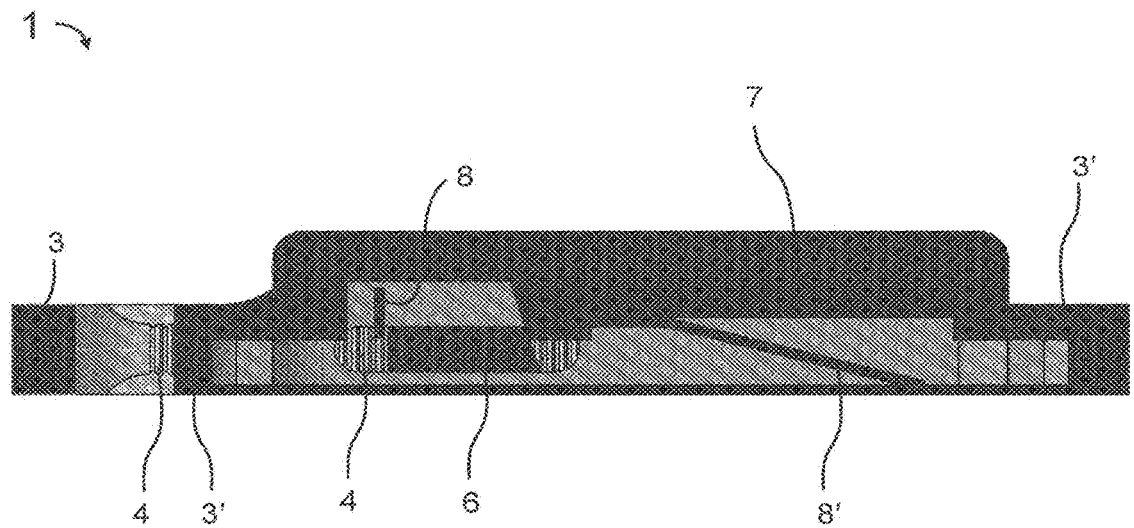
FIG. 5B shows a cross sectional side view of the subcutaneous bone distraction device of FIG. 1.

The push button expansion system 5'-6-7-8-8' described above is shown in cutaway perspective view in FIG. 5A, and in cross sectional view in FIG. 5B.

Figure 6A:
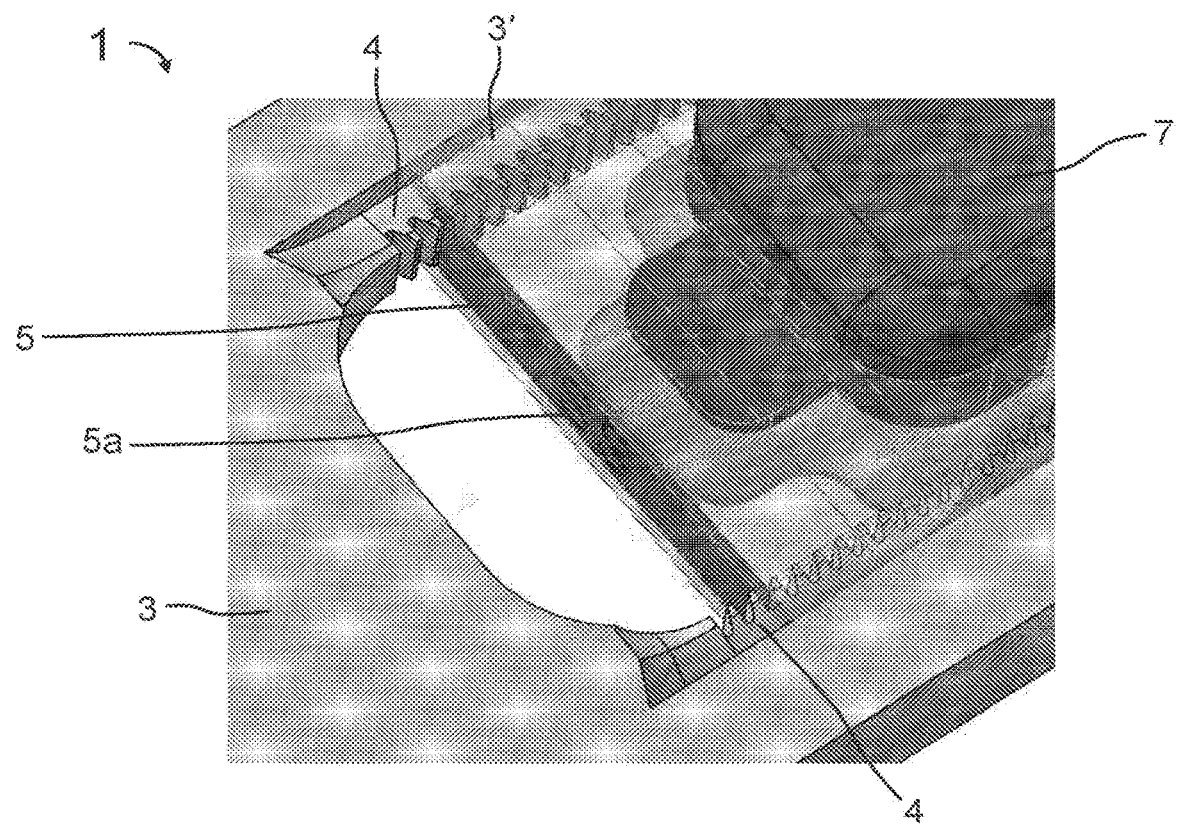
FIG. 6A shows a transparent perspective top view of a portion of the subcutaneous bone distraction device of FIG. 1.
Figure 6B:
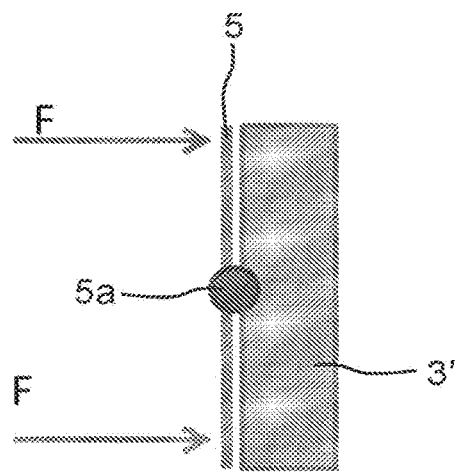
FIGS. 6B and 6C show forces applied to the first locking pawl at rest (FIG. 6B) and upon activation of the expansion system (FIG. 6C) of the subcutaneous bone distraction device of FIG. 1.
Figure 6C:
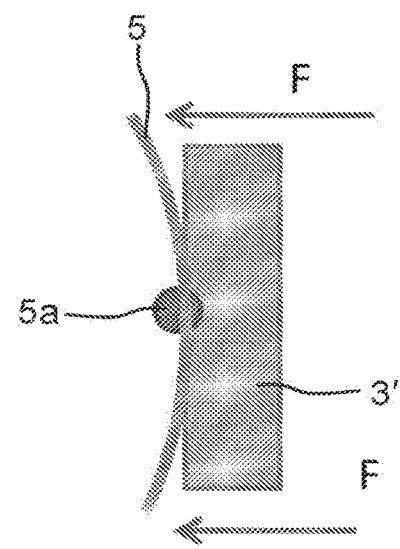

As shown in FIG. 6A, the first locking pawl 5 may be attached to the end of the second block portion 3' by one or more pawl anchors 5a. The one or more pawl anchors 5a are generally located at or near the midline of the first locking pawl 5 so that the ends of the first locking pawl 5 can flex away from the end of the second block portion 3' as shown in FIG. 6C. This arrangement also prevents the second block portion 3' from regressing toward the first block portion 3 as shown in FIG. 6B.

In some embodiments, the subcutaneous bone distraction device 1 further comprises at least one sensor. In general, the at least one sensor is in wireless communication with a data receiver 1000 that converts the wireless signal from the at least one sensor into readable information about the growth of callus bone between the first bone segment 2 and the second bone segment 2' and/or about the position of the second block portion 3' relative to the first block portion 3. In some embodiments, the data receiver 1000 stores information about each activation of the expansion system 5'-6-7-8-8' including, for example, the date and time of each activation, the length of each distraction, the total length of distraction, and/or the total number of distractions. In some embodiments, the data receiver 1000 transmits a signal to a user device when the wireless signal(s) from the at least one sensor corresponds to a growth of the callus bone sufficient to warrant an additional activation of the expansion system 5'-6-7-8-8'.

Figure 7:
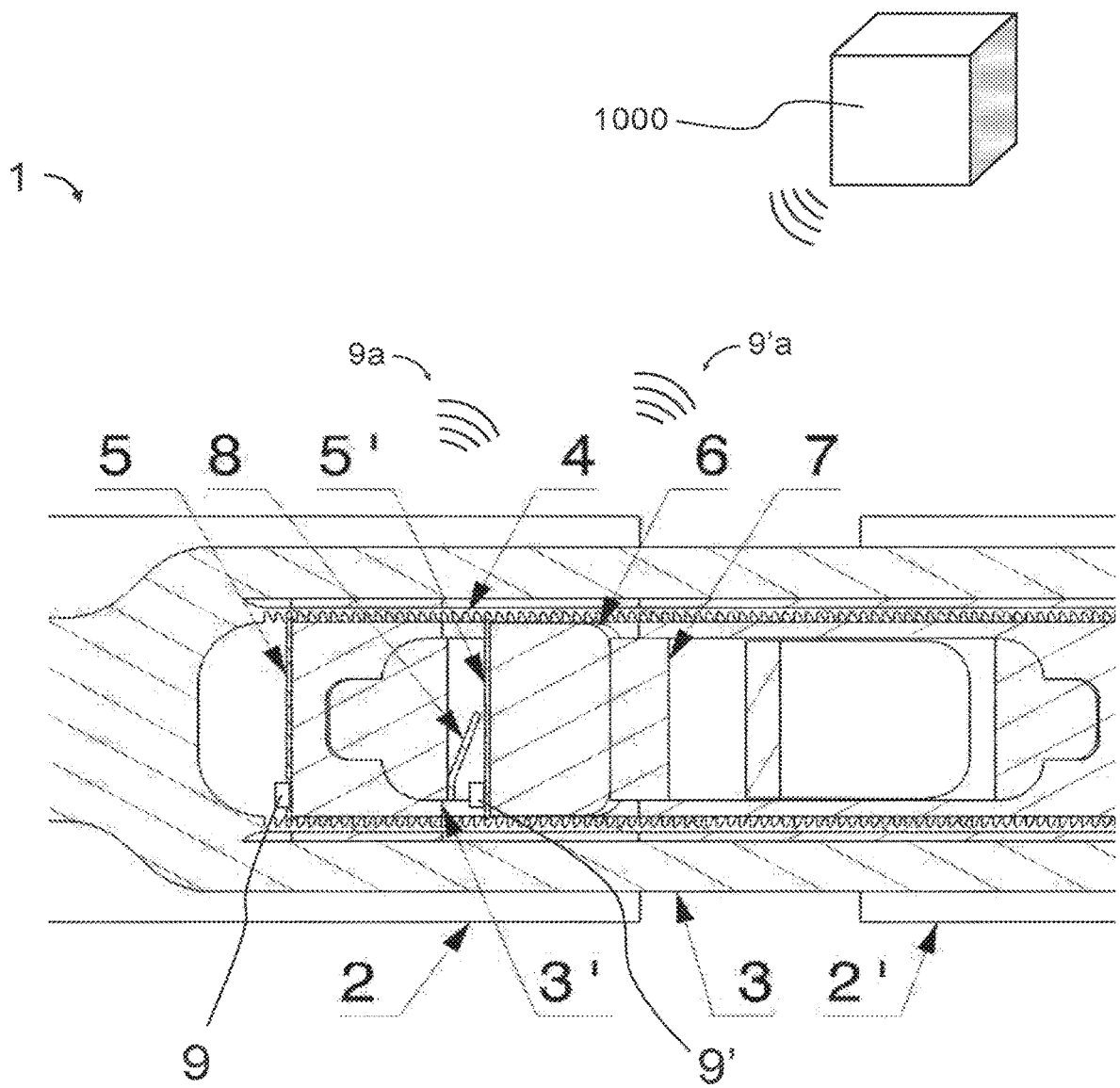
FIG. 7 shows a cross sectional top view of a portion of the subcutaneous bone distraction device of FIG. 1 including a sensor for determining the right positioning of the locking pawl.

As shown in FIG. 7, a subcutaneous bone distraction device 1 consistent with one embodiment of the present disclosure includes a first sensor 9 and a second sensor 9'. In this embodiment, the first sensor 9 may be associated with the first locking pawl 5 and may comprise a piezoresistive sensor in wireless communication 9a with the data receiver 1000. The first sensor 9 provides data about the advancement of the first locking pawl 5 from one ratchet position to a subsequent ratchet position. For example, movement of the first locking pawl 5 from an initial ratchet position to the next adjacent ratchet position creates vibration in the first locking pawl 5 that is converted into a wireless electrical signal 9a by the first sensor 9. The second sensor 9' may be associated with the second locking pawl 5' and may comprise a piezoresistive sensor in wireless communication 9'a with the data receiver 1000. When the second locking pawl advances from an initial ratchet position to the next adjacent ratchet position, vibrations in the second locking pawl 5' induce an electrical signal in the second sensor 9' that is transmitted 9'a to the data receiver 1000. The data receiver 1000 interprets the signal as indicating that the floating element 6 has returned to its resting state, and that the subcutaneous bone distraction device 1 is ready for a subsequent distraction step.

Figure 8:
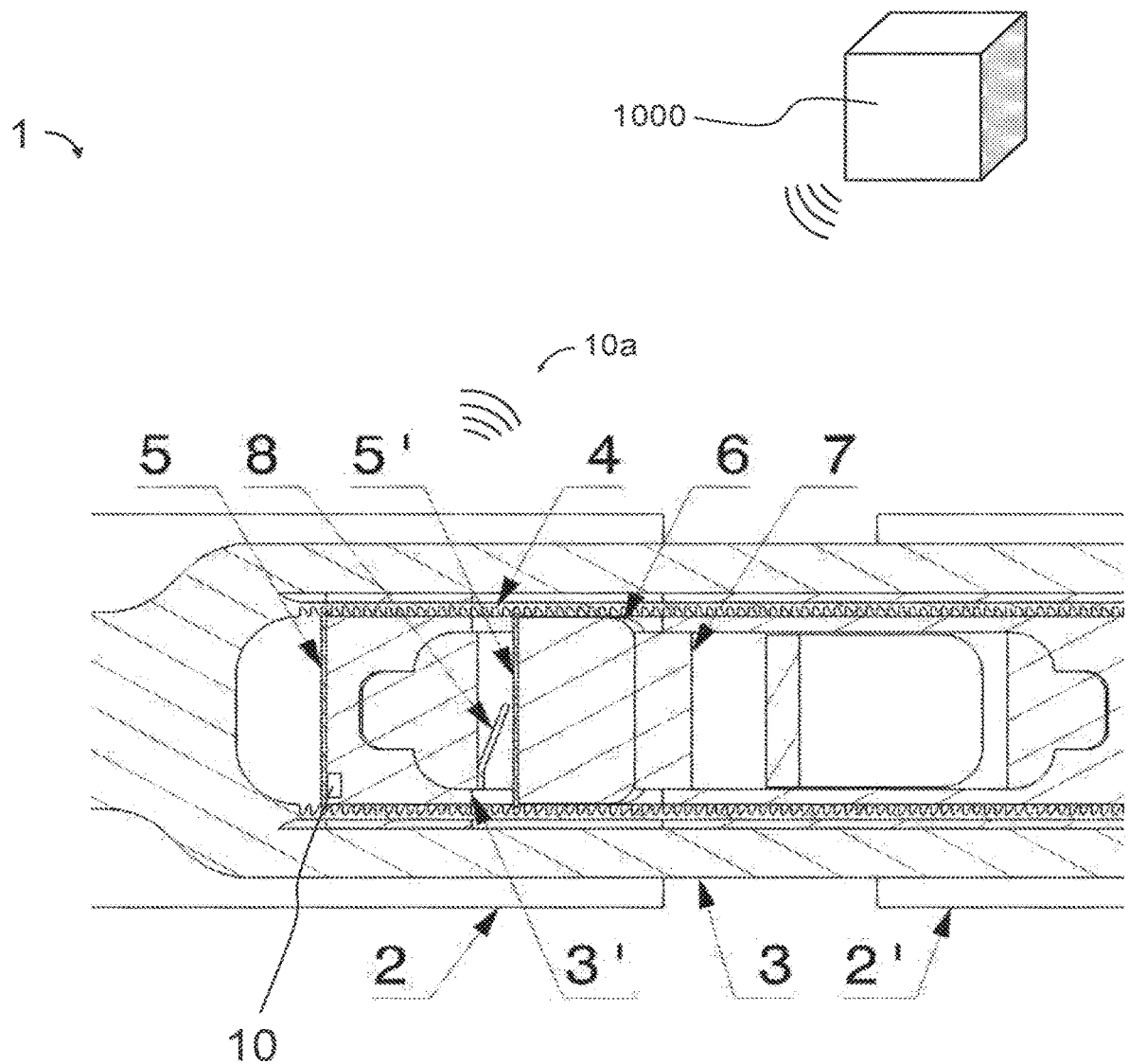
FIG. 8 shows a cross sectional top view of a portion of the subcutaneous bone distraction device of FIG. 1 including a sensor for determining the right positioning of the locking pawl.

Referring now to FIG. 8, a subcutaneous bone distraction device 1 consistent with one embodiment of the present disclosure may include a sensor 10 associated with the end of the second block portion 3' nearest the first locking pawl 5. In such an embodiment, the sensor 10 determines a mechanical constraint on the first locking pawl 5 upon which the lateral force is applied by the downward force exerted on the actuator 7. The mechanical constraint correlates to the degree of expansion along each incremental advancement of the second block portion 3". More specifically, a high mechanical constraint corresponds to a small advancement of the second block portion 3' along the incremental expansion; a low mechanical constraint corresponds to a complete or near-complete advancement of the second block portion 3' along the incremental expansion and indicates that another distraction event (e.g., a subsequent applied force to the actuator 7) may be made by the user.

Figure 9:
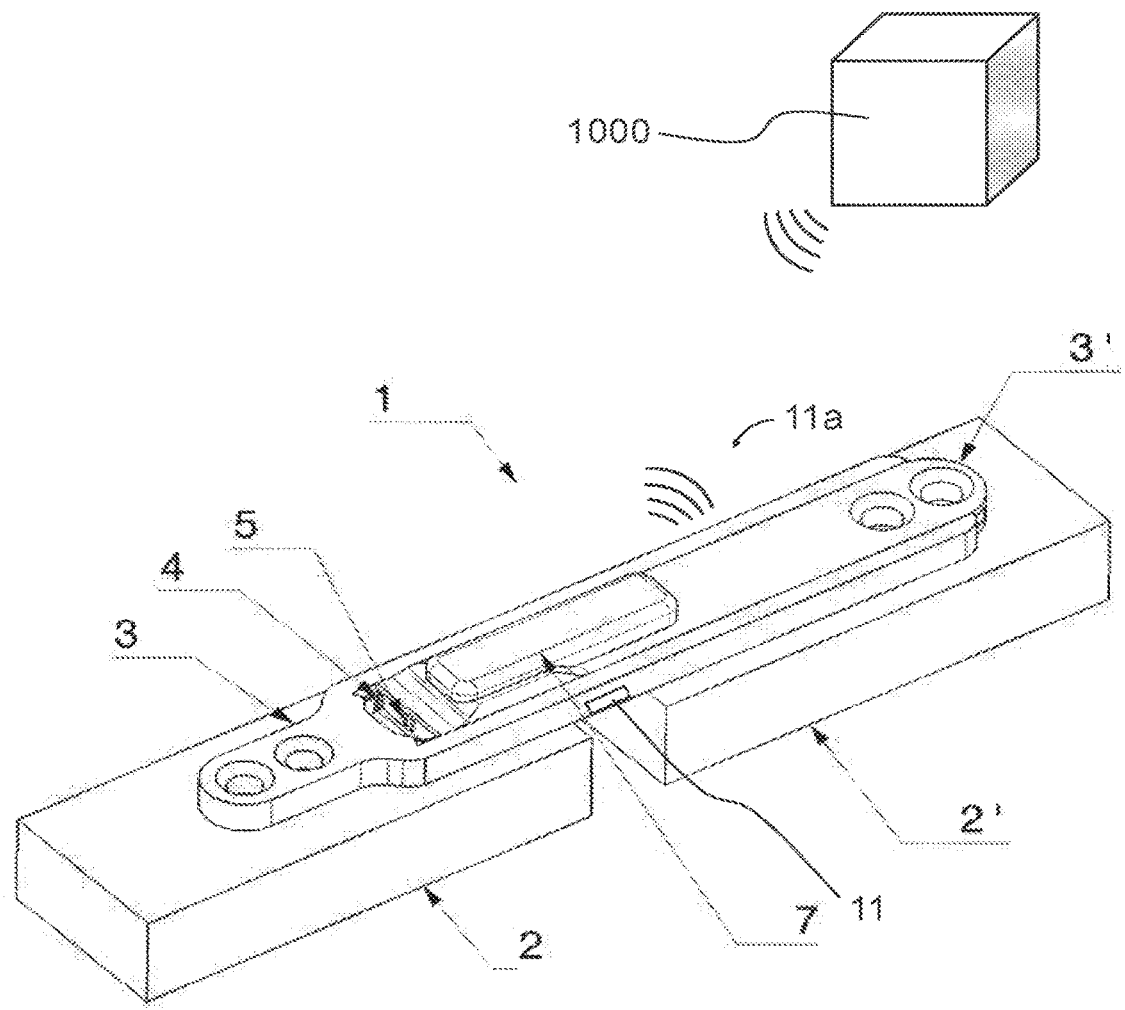
FIG. 9 shows a perspective view of a portion of the subcutaneous bone distraction device of FIG. 1 including a sensor for determining callus formation between two bone segments according to another embodiment of the present disclosure.

As shown in FIG. 9, a subcutaneous bone distraction device 1 consistent with one embodiment of the present disclosure comprises a sensor 11 disposed on the first block portion 3 and/or on the second block portion 3', and may be aligned with the gap between the first bone segment 2 and the second bone segment 2'. In such an embodiment, the sensor 11 determines a level of callus bone formation between the first bone segment 2 and the second bone segment 2' and communicates via wireless signal to the data receiver 1000. In some embodiments, the sensor 11 is one, two or three of: a vibration senor, an acoustic emission sensor, and a dielectric sensor. Electrical signals induced in the sensor 11 that correspond to stiffer callus bone formation indicate that a subsequent distraction event (e.g., a subsequent downward force to the actuator 7) may be initiated by the user.

Figure 10:
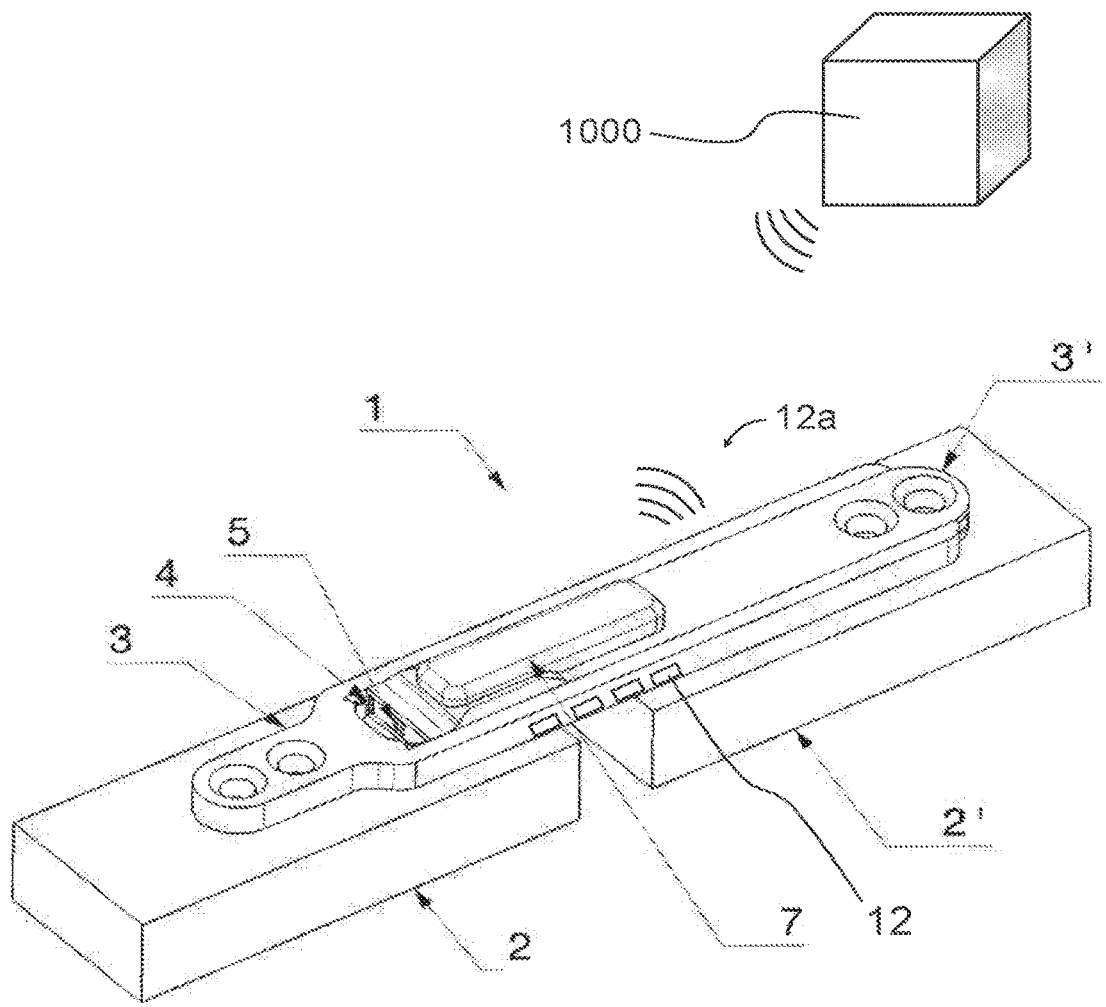
FIG. 10 shows a perspective view of a portion of the subcutaneous bone distraction device of FIG. 1 including a sensor for determining callus formation between two bone segments according to another embodiment of the present disclosure.

Referring now to FIG. 10, a plurality of bone sensors 12 may be positioned on the first block portion 3 and/or on the second block portion 3', and may be disposed along the gap between the first bone segment 2 and the second bone segment 2'. In such an embodiment, each of the plurality of sensors 12 communicate wirelessly with the data receiver 1000 to provide information about the growth of callus bone between the first bone segment 2 and the second bone segment 2'. Electrical signals corresponding to stiffer callus bone formation in the gap indicate that a subsequent distraction event (e.g., a subsequent downward force to the actuator 7) may be initiated by the user.

In one embodiment, a subcutaneous bone distraction device 1 includes more than one type of sensor. In one embodiment, a subcutaneous bone distraction device 1 consistent with the present disclosure includes first sensor 9 and second sensor 9' associated with the first locking pawl 5 and the second locking pawl 2', respectively, and sensor 10 associated with the end of the second block portion 3' nearest the first locking pawl 5 as described above. In another embodiment, a subcutaneous bone distraction device 1 consistent with the present disclosure includes first sensor 9 and second sensor 9' associated with the first locking pawl 5 and the second locking pawl 2', respectively, and sensor 11 disposed on the first block portion 3 and/or on the second block portion 3' as described above. In another embodiment, a subcutaneous bone distraction device 1 consistent with the present disclosure includes first sensor 9 and second sensor 9' associated with the first locking pawl 5 and the second locking pawl 2', respectively, and plurality of bone sensors 12 positioned on the first block portion 3 and/or on the second block portion 3' as described above.

In another embodiment, a subcutaneous bone distraction device 1 consistent with the present disclosure includes sensor 10 associated with the end of the second block portion 3' nearest the first locking pawl 5 and sensor 11 disposed on the first block portion 3 and/or on the second block portion 3' as described above. In another embodiment, a subcutaneous bone distraction device 1 consistent with the present disclosure includes sensor 10 associated with the end of the second block portion 3' nearest the first locking pawl 5 and plurality of bone sensors 12 positioned on the first block portion 3 and/or on the second block portion 3' as described above.

In another embodiment, a subcutaneous bone distraction device 1 consistent with the present disclosure includes sensor 11 disposed on the first block portion 3 and/or on the second block portion 3' and plurality of bone sensors 12 positioned on the first block portion 3 and/or on the second block portion 3' as described above.

In any embodiment disclosed herein, the first block portion 3 and the second block portion 3' may be made of any suitable bio-compatible material. In some embodiments, the first block portion 3 and the second block portion 3' comprise, consist essentially of, or consist of titanium, stainless steel, an titanium alloy, a non-titanium metallic alloy, a polymeric material, a plastic, a plastic composite, polyether ether ketone (PEEK), ceramic, and/or an elastic material.

In some embodiments, a protective membrane surrounds the bone distraction device 1. The protective membrane may be any biocompatible and flexible material, such as silicone or polytetrafluoroethylene (PTFE), that allows the bone distraction device 1 to expand without breaching and exposing the push button expansion system 5'-6-7-8-8' to the forming callus bone.

In some embodiments, the present disclosure provides a subcutaneous bone distraction device 1 comprising: a first block portion 3 including a pair of opposing rails 3a and a pair of opposing ratchet sections 4; and a second block portion 3' that slidably mates with the first block portion 3 and includes a first locking pawl 5 and a push button expansion system 5'-6-7-8-8' for incrementally and slidably advancing the second block portion 3' along the pair of opposing rails 3a of the first block portion 3. In some embodiments, the first block portion 3 further comprises at least one anchor hole 20 disposed through a thickness of the first block portion 3 for anchoring the first block portion 3 to a first section of bone 2. In some embodiments, the second block portion 3' further comprises at least one anchor hole 20 disposed through a thickness of the second block portion 3' for anchoring the second block portion 3' to a second section of bone 2', wherein the second section of bone 2' is separated from the first section of bone 2 by a gap. In some embodiments, the push button expansion system 5'-6-7-8-8' comprises an actuator 7 for receiving input from a user, a floating element 6 for transferring input from the actuator 7 into lateral motion, a second locking pawl 5' associated with the floating element 6 and with the pair of opposing ratchet sections 4 of the first block portion 3, a first energy storage element 8 associated with the floating element 6 for returning the floating element 6 to its initial position, and a second energy storage element 8' for returning the actuator 7 to its initial position after the lateral slidable motion has completed. In some embodiments, each activation of the expansion system 5'-6-7-8-8' expands the second block portion 3' along the pair of opposing rails 3a by no more than about 0.25 mm. In some embodiments, each activation of the expansion system 5'-6-7-8-8' expands the second block portion 3' along the pair of opposing rails 3a by no more than about 0.2 mm. In some embodiments, each activation of the expansion system 5'-6-7-8-8' expands the second block portion 3' along the pair of opposing rails 3a by no more than about 0.15 mm. In some embodiments, each activation of the expansion system 5'-6-7-8-8' expands the second block portion 3' along the pair of opposing rails 3a by no more than about 0.1 mm. In some embodiments, the subcutaneous bone distraction device 1 further comprises at least one sensor in wireless communication with a data receiving device 1000 and for determining extent of callus growth between a first bone section 2 and a second bone section 2'. In some embodiments, the at least one sensor comprises a first sensor 9 associated with the first locking pawl 5 and a second sensor 9' associated with the second locking pawl 5'. In some embodiments, the at least one sensor comprises a force sensor 10 associated with the first locking pawl 5. In some embodiments, the at least one sensor comprises a bone regeneration sensor associated with the first block portion 3 or with the second block portion 3' for determining callus stiffness. In some embodiments, the bone regeneration sensor 11 is a vibration sensor. In some embodiments, the bone regeneration sensor 11 is an acoustic emission sensor. In some embodiments, the bone regeneration sensor 11 is a dielectric sensor. In some embodiments, the at least one sensor comprises a plurality of bone regeneration sensors 12 associated with the first block portion 3 or with the second block portion 3'. In some embodiments, the plurality of bone regeneration sensors 12 is positioned along a length of the first block portion 3 or along a length of the second block portion 3'. In some embodiments, the first block portion 3 is for anchoring to a first bone section 2, wherein the second block portion 3' is for anchoring to a second bone portion 2', and wherein the first bone portion 2 and the second bone portion 2' are separated by a gap. In some embodiments, the subcutaneous bone distraction device 1 further comprises a protective membrane around the bone distraction device 1.

Figure 11:
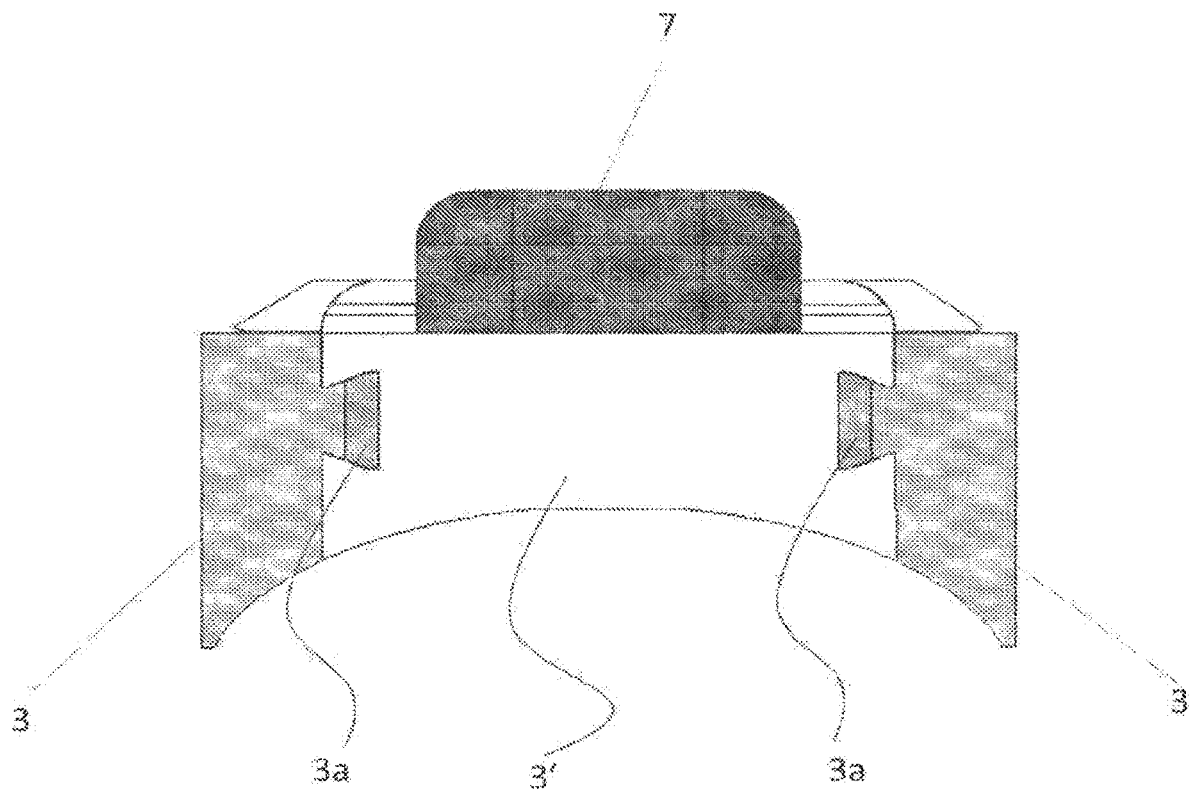
FIG. 11 shows an end view of a subcutaneous bone distraction device including a protective membrane across the gap formed and/or expanded between the first block portion 3 and the second block portion 3'.

Referring now to FIG. 11, a bone distraction device 1 consistent with the present disclosure may further include one or more protective membranes 30a,30b for protecting a gap formed between the first block portion 3 and the second block portion 3' during use of the bone distraction device 1. Such embodiments of a bone distraction device 1 may be particularly useful for preventing soft tissue from growing into the gap that expands between the first block portion 3 and the second block portion 3' as the second block portion 3' is advanced over time. In some embodiments, the one or more protective membranes 30a,30b are attached to the second block portion 3' and slide along the first block portion 3. The one or more protective membranes 30a,30b may be formed of any biocompatible material.

2. Methods of Lengthening Bone Using Subcutaneous Push-Button Bone Distraction Devices Subcutaneous bone distraction devices 1 consistent with the present disclosure are useful for lengthening a bone of a subject, such as a human subject.

Generally, methods of lengthening bone disclosed herein comprise implanting a subcutaneous bone distraction device 1 to two adjacent bone segments and completely under the skin of a subject, and periodically applying an actuating force to the subcutaneous bone distraction device 1 to expand the subcutaneous bone distraction device 1 in a single direction. In some embodiments, the method further comprises creating a gap in a bone to form two adjacent bone segments (e.g., osteotomy or corticotomy) before implanting the subcutaneous bone distraction device 1.

In some embodiments, the subcutaneous bone distraction device 1 comprises a first block portion 3 and a second block portion 3' that is slidably mated to the first block portion 3. The method of lengthening a bine using such a subcutaneous bone distraction device 1 comprises anchoring the first block portion 3 to a first segment of bone 2, and anchoring the second block portion 2 to a second segment of bone 2'. In some embodiments, the first block portion 3 is anchored to the first bone segment 2, and the second block portion 3' is thereafter slidably mated to the first block portion 3 before the second block portion 3' is anchored to the second bone segment 2'. In another embodiment, the second block portion 3' is anchored to the second bone segment 2', and the first block portion 3 is thereafter slidably mated to the second block portion 3' before the first block portion 3 is anchored to the first bone segment. In another embodiment, the first block portion 3 and the second block portion 3' are slidably mated together before one block portion (e.g., the first block portion 3) is anchored to one bone segment (e.g., the first bone segment 2) before the other block portion (e.g., the second block portion 3') is anchored to the other bone segment (e.g., the second bone segment 2').

Once anchored to the two adjacent bone segments, the subcutaneous bone distraction device 1 is actuated in a series of repeated cycles. In general, each cycle comprises steps of: causing the subcutaneous bone distraction device 1 to expand in a single direction substantially parallel to the long dimension of the bone segments, and waiting for callus bone to form between the two adjacent bone segments.

Causing the subcutaneous bone distraction device 1 to expand is generally accomplished by applying a force to the push button expansion system 5'-6-7-8-8' of the subcutaneous bone distraction device 1. For example, in the embodiments shown in FIGS. 1-6A and 7-10, a downward force applied to the actuator 7 causes the second block portion 3' to expand laterally away from the first block portion 3 by a predetermined distance (e.g., 0.25 mm).

In some embodiments, such as embodiments in which the subcutaneous bone distraction device 1 additionally includes one or more sensors 9, 9', 10, 11 and/or 12, the step of waiting for callus bone to grow between the first bone segment 2 and the second bone segment 2' may comprise obtaining data from the sensor about callus bone growth progress and/or the degree of expansion of the second block portion 3' from the first block portion 3 before causing the subcutaneous bone distraction device 1 to expand in a subsequent cycle.

Once the bone has been lengthened to the desired extent, the method may optionally include removing the subcutaneous bone distraction device 1 from the subject.

The methods disclosed herein may be used to distract any suitable bone, but are particularly suited for distracting small bones of an adult (e.g., a bone of an adult's foot or hand), and limb bones of a child or baby.

In one embodiment, the present disclosure provides a method of lengthening a bone in a subject, the method comprising: anchoring a first block portion 3 of a subcutaneous bone distraction device 1 to a first bone section 2; anchoring a second block portion 3' of a subcutaneous bone distraction device 1 to a second bone section 2': actuating a push button expansion system 5'-6-7-8-8' to incrementally and slidably advance the second block portion 3' along a pair of opposing rails 3a of the first block portion 3; waiting a length of time; thereafter actuating the push button expansion system 5'-6-7-8-8' to incrementally and slidably advance the second block portion 3' along the pair of opposing rails 3a of the first block portion 3; and repeating the steps of waiting a length of time and thereafter actuating the expansion system until the bone has been lengthened to a desired length. In some embodiments, the method further comprises determining an extent of callus growth between the first bone section 2 and the second bone section 2' after the step of actuating the push button expansion system 5'-6-7-8-8' and the step of thereafter actuating the push button expansion system 5'-6-7-8-8', wherein the step of thereafter actuating the push button expansion system 5'-6-7-8-8' occurs only after the extent of callus growth is determined to be sufficient. In some embodiments, the first block portion 3 includes a pair of opposed ratchets 4 for enabling incremental advancement of the second block portion 3' upon activation of the push button expansion system 5'-6-7-8-8'. In some embodiments, the second block portion 3' further comprises a first locking pawl 5 for engaging the pair of opposed ratchets 4. In some embodiments, the push button expansion system 5'-6-7-8-8' comprises an actuator 7 for receiving an activation force from a user, a floating element 6 for transferring input from the actuator 7 into lateral motion, a second locking pawl 5' associated with the floating element 6 and with the pair of opposing ratchet sections 4 of the first block portion 3, a first energy storage element 8 associated with the floating element 6 for returning the floating element 6 to its initial position, and a second energy storage element 8' for returning the actuator 7 to its initial position after receiving input from the user. In some embodiments, each activation of the push button expansion system 5'-6-7-8-8' expands the second block portion 3' along the pair of opposing rails 3a by no more than about 0.25 mm. In some embodiments, each activation of the push button expansion system 5'-6-7-8-8' expands the second block portion 3' along the pair of opposing rails 3a by no more than about 0.2 mm. In some embodiments, each activation of the push button expansion system 5'-6-7-8-8' expands the second block portion 3' along the pair of opposing rails 3a by no more than about 0.15 mm. In some embodiments, each activation of the push button expansion system 5'-6-7-8-8' expands the second block portion 3' along the pair of opposing rails 3a by no more than about 0.1 mm. In some embodiments, the step of determining the extent of callus growth comprises obtaining callus stiffness information from at least one sensor in wireless communication with a data receiving device. In some embodiments, the at least one sensor comprises a first sensor 9 associated with the first locking pawl 5 and a second sensor 9' associated with the second locking pawl 5'. In some embodiments, the at least one sensor comprises a force sensor 10 associated with the first locking pawl 5. In some embodiments, the at least one sensor comprises a bone regeneration sensor 11 associated with the first block portion 3 or with the second block portion 3' for determining callus stiffness. In some embodiments, the bone regeneration sensor 11 is a vibration sensor. In some embodiments, the bone regeneration sensor 11 is an acoustic emission sensor. In some embodiments, the bone regeneration sensor 11 is a dielectric sensor. In some embodiments, the at least one sensor comprises a plurality of bone regeneration sensors 12 associated with the first block portion 3 or with the second block portion 3'. In some embodiments, the plurality of bone regeneration sensors 12 is positioned along a length of the first block portion 3 or along a length of the second block portion 3'. In some embodiments, the method further comprises performing osteotomy on the bone before the steps of anchoring a first block portion 3 of a subcutaneous bone distraction device 1 to a first bone section 2 and anchoring a second block portion 3' of a subcutaneous bone distraction device 1 to a second bone section 2'. In some embodiments, the method further comprises, after the bone has been lengthened to a desired length, removing the first block portion 3 from the first bone section 2 and removing the second block portion 3' from the second bone portion 2'. In some embodiments, the bone is a small bone. In some embodiments, the small bone is a bone of a hand. In some embodiments, the bone is a bone of a foot. In some embodiments, the subject is a child. In some embodiments, the subject is an adolescent. In some embodiments, the subject is an adult.

Referring generally to FIGS. 12-23, the present disclosure provides modular devices and methods for lengthening a bone of a subject, especially a bone of a child or adolescent or a small bone of an adult such as a bone of a hand or a foot.

3. Modular Bone Distraction Devices

Referring generally to FIGS. 12-23, bone distraction devices 2100 consistent with some embodiments of the present disclosure generally comprise a first block portion 2103 for anchoring to a first bone segment 2102, a second block portion 2103' for anchoring to a second bone segment 2102', and a remotely-actuated expansion system 2107 that enables the bone distraction devices 2100 to expand in a single direction upon remote input from a user. The first bone segment 2102 should be in close enough proximity to the second bone segment 2102' that callus bone will grow between the two bone segments. The first block portion 2103 and the second block portion 2103' interconnect in a manner that allows the bone distraction devices 2100 to slidably expand. In some embodiments, the bone distraction device 2100 slidably expands, but is configured to prevent the bone distraction device 2100 from slidably contracting after anchoring to the first bone segment 2102 and to the second bone segment 2102".

Figure 12:
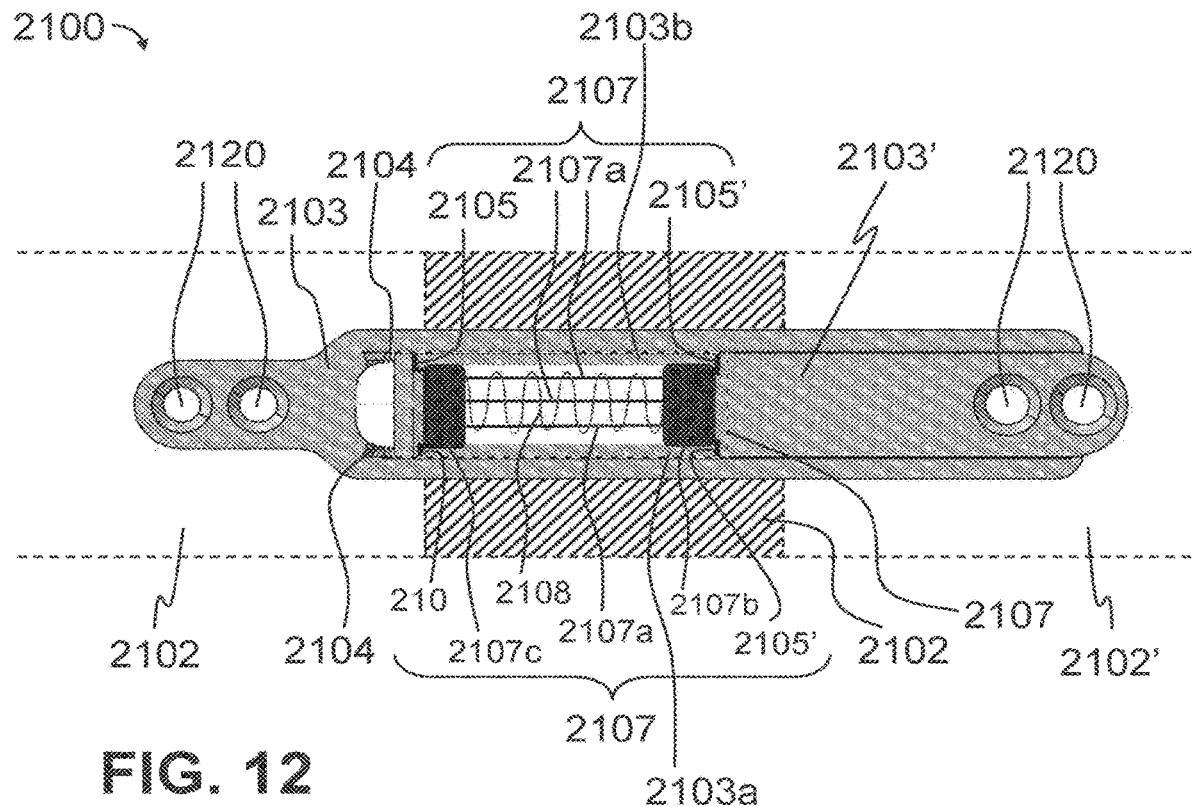
FIG. 12 shows a partial cutaway view of a remote-actuated bone distraction device anchored to two bone segments according to one embodiment of the present disclosure.

Referring now to FIG. 12, a bone distraction device 2100 according to some embodiments of the present disclosure comprises a first block portion 2103, a second block portion 2103' slidably associated with the first block portion 2103, and a remotely-actuated expansion system 2107 that controls movement of the second block portion 2103' relative to the first block portion 2103.

The first block portion 2103 may include one or more anchor holes 2120 for securing the first block portion 2103 to a first bone segment 2102 using any suitable fastener such as a surgical screw (not shown). In some embodiments, the first block portion 2103 includes at least two anchor holes 2120.

The first block portion 2103 may further include a ratchet 2104 for enabling incremental expansion of the bone distraction device 2100 upon input from a user. In some embodiments, the ratchet 2104 includes a plurality of teeth that are spaced at a constant distance to provide even incremental expansion of the subcutaneous bone distraction device 2100 with each input by the user. In some embodiments, the spacing between the plurality of teeth is about 0.1 mm to 0.5 mm, for example about 0.1 mm, about 0.15 mm, about 0.2 mm, about 0.25 mm, about 0.3 mm, about 0.35 mm, about 0.4 mm, about 0.45 mm, or about 0.5 mm. In some embodiments, the spacing between the plurality of teeth is about 0.25 mm.

In other embodiments, the ratchet 2104 includes a plurality of teeth spaced at varying distances to enable incremental expansion of the bone distraction device 2100 with subsequent inputs by the user. For example and without limitation, in some embodiments the ratchet 4 may include teeth spaced at repeating intervals of about 0.25 mm, 0.25 mm, 0.25 mm, 0.5 mm, 0.25 mm, 0.25 mm, 0.25 mm, 0.5 mm, etc. In such embodiments, the larger interval enables the user to expand the bone distraction device 2100 just once before an overnight rest period without being forced to wake before dawn to provide an additional input to expand the bone distraction device 2100.

The second block portion 2103' includes one or more anchor holes 2120 for securing the second block portion 2103' to a second bone segment 2102' using any suitable fastener such as a surgical screw (not shown). In some embodiments, the first block portion 2103 includes at least two anchor holes 2120.

The remotely-actuated expansion system 2107 includes a first floating element 2107b including at least one pair of first locking pawls 2105', a second floating element 2103" including at least one pair of second locking pawls 2105, at least one length of shape memory alloy 2107a expandably linking the first floating element 2107b and the second floating element 2107c, and a spring 2108 for reducing the space between the first floating element 2107b and the second floating element 2107c. In some embodiments, the remotely-actuated expansion system 2107 is removable from the second block portion 2103".

The first locking pawls 2105' engage with the ratchet 2104 to allow the first floating element 2107b to advance along the ratchet 2104 in a single direction. Similarly, the second locking pawls 2105 engage with the ratchet 2104 to allow the first floating element 2107b to advance along the ratchet 2104 in a single direction, namely the same direction as the first locking pawls 2105'.

The at least one length of shape memory alloy 2107a connects the first floating element 2107b and the second floating element 2107c. In some embodiments, the at least one length of shape memory alloy 2107a comprises a single length of shape memory alloy 2107a connecting the first floating element 2107b and the second floating element 2107c. In other embodiments, the at least one length of shape memory alloy 2107a comprises two lengths of shape memory alloy 2107a connecting the first floating element 2107b and the second floating element 2107c. In other embodiments, such as the embodiment shown in FIG. 12, the at least one length of shape memory alloy 2107a comprises three lengths of shape memory alloy 2107a connecting the first floating element 2107b and the second floating element 2107c. In other embodiments, the at least one length of shape memory alloy 2107a comprises more than three lengths of shape memory alloy 2107a connecting the first floating element 2107b and the second floating element 2107c.

In embodiments featuring more than one length of shape memory alloy 2107a connecting the first floating element 2107b and the second floating element 2107c, the more than one length of shape memory alloy 2107a may comprise a single piece of shape memory alloy 2107a that is wound back and forth between the first floating element 2107b and the second floating element 2107c. In other embodiments, each length of shape memory alloy 2107a connecting the first floating element 2107b and the second floating element 2107c is a separate piece of shape memory alloy 2107a. In still other embodiments, at least two lengths of shape memory alloy 2107a connecting the first floating element 2107b and the second floating element 2107c comprise a single piece of shape memory alloy, while at least one other length of shape memory alloy 2107a connecting the first floating element 2107b and the second floating element 2107c comprise a separate piece of shape memory alloy.

Remote-actuated expansion systems 2107 that include more than one length of shape memory alloy 2107a provide additional stability in the sliding motion of the second block portion 2103' relative to the first block portion 2103. For example, the risk of one side of the remote-actuated expansion system 2107 advancing incrementally along the ratchet 2104 without the other side of the remote-actuated expansion system 2107 also advancing along the ratchet 2104 is significantly lower when the remote-actuated expansion system 2107 includes more than one length of shape memory alloy 2107a connecting the first floating element 2107b and the second floating element 2107c, compared to a similar embodiment that includes only a single length of shape memory alloy 2107a connecting the first floating element 2107b and the second floating element 2107c.

Remote-actuated expansion systems 2107 that include more than one length of shape memory alloy 2107a also enable bone distraction devices 2100 according to the present disclosure to feature a profile shape (e.g., a cross-sectional shape orthogonal to the direction of distraction) that is curved, rather than linear as shown in FIG. 12.

Remote-actuated expansion systems 2107 that include more than one length of shape memory alloy 2107a also enable bone distraction devices 2100 according to the present disclosure to feature a path of distraction that is curved, rather than linear as shown in FIG. 12. In such embodiments, the first block portion 2103 may include a generally curved shape along the direction of the ratchets 2104. The multiple lengths of shape memory alloy 2107a in the remote-activated expansion system 2107 may feature different lengths in such embodiments, for example with a first relatively short length of shape memory alloy 2107a disposed nearest the ratchet 2104 having the shorter radius, and a second relatively long length of shape memory alloy 2107a disposed nearest the ratchet 2104 having the longer radius. Additional lengths of shape memory alloy 2107a having intermediate lengths may be disposed between the first relatively short length of shape memory alloy 2107a and the second relatively long length of shape memory alloy 2107a in some embodiments.

The spring 2108 connects the first floating element 2107b and the second floating element 2107c, and functions to reduce the gap between the first floating element 2107b and the second floating element 2107c. In some embodiments, a single spring 2108 connects the first floating element 2107b and the second floating element 2107c. In other embodiments, more than one spring 2108, such as two springs 2108, three springs 2108, four springs 2108, five springs 2108, or more than five springs 2108 connect the first floating element 2107b and the second floating element 2107c.

The first floating element 2107b is adjacent to the second block portion 2103', and includes a first pair of locking pawls 2105' that engages with the ratchet 2104 to provide incremental expansion of the bone distraction device 2100 along the length of the first block portion 2103. In some embodiments, the first pair of locking pawls 2105' comprises a unitary flexible plate that is free to flex in one direction to allow the first floating element 2107b to slide in one direction against the first block portion 2103, but is not free to flex in the opposite direction, preventing the first floating element 2107b from sliding in the opposite direction against the first block portion 2103. In other embodiments, the first pair of locking pawls 2105' comprises two individual pawls: one on each side of the remotely-actuated expansion system 2107 as shown in FIG. 12.

The second floating element 2107c is disposed in the remote-actuated expansion system 2107 opposite the first floating element 2107b, and includes a second pair of locking pawls 2105 that engages with the ratchet 2104 to provide incremental expansion of the bone distraction device 2100 along the length of the first block portion 2103. In some embodiments, the second pair of locking pawls 2105 comprises a unitary flexible plate that is free to flex in one direction to allow the second floating element 2107c to slide in one direction against the first block portion 2103, but is not free to flex in the opposite direction, preventing the second floating element 2107c from sliding in the opposite direction against the first block portion 2103. In other embodiments, the second pair of locking pawls 2105 comprises two individual pawls; one on each side of the remotely-actuated expansion system 2107 as shown in FIG. 12.

The remote-actuated expansion system 2107 may further include a phase change material placed at the extremities or surroundings the shape memory alloy 2107a. The phase change material absorbs excess heat from the activated shape memory alloy 2107a to reduce or eliminate the risk of tissue burns from heat liberated from the shape memory alloy 2107a. In some embodiments, the phase change material consists or consists essentially of a biocompatible phase change material, such as a paraffin. In other embodiments, the phase change material comprises a non-biocompatible phase change material; in such embodiments the phase change material is encapsulated to prevent contact between the phase change material and tissue of the subject. The phase change material may be any suitable substance that has a melting point similar to the transition temperature of the shape memory alloy 2107a. For example, in some embodiments, the phase change material may be an organic phase change material with a melting point of about 50° C. to about 90° C., such as paraffin 24-carbons, paraffin 25-carbons, paraffin 26-carbons, paraffin 27-carbons, paraffin 28-carbons, paraffin 29-carbons, paraffin 30-carbons, paraffin 31-carbons, paraffin 32-carbons, paraffin 33-carbons, paraffin 34-carbons, camphene, O-nitroaniline, 9-heptadecanone, thymol, methyl behenate, diphenyl amine, p-dichlorobenzene, hypophosphoric acid, o-xylene dichloride, ß-chloroacetic acid, chloroacetic acid, nitro naphthalene, heptadecanoic acid, a-chloroacetic acid, bees wax, glycolic acid, p-bromophenol, azobenzene, acrylic acid, 2,4-dinitrotoluene, phenylacetic acid, thiosinamine, bromocamphor, durene, methyl bromobenzoate, pentadecanoic acid, tristearin, myristic acid, palmitic acid, stearic acid, or acetamide. In some embodiments, the phase change material is an inorganic phase change material such as Na2SiO3·5H2O. In some embodiments, the phase change material is a commercially available phase change material by Phase Change Energy Solutions, such as: 0500-Q50 BioPCM, 0500-Q52 BioPCM, 0500-Q54 BioPCM, 0500-Q56 BioPCM, 0500-Q58 BioPCM, 0500-Q62 BioPCM, 0500-Q65 BioPCM, 0500-Q68 BioPCM, 0500-Q70 BioPCM, 0500-Q72 BioPCM, 0500-Q76 BioPCM, or 0500-Q79 BioPCM. In some embodiments, the phase change material is a commercially available phase change material by Pluss, such as: savE OM 50, savE OM 55, savE OM 65, savE FSM 65, or savE HS 89. In some embodiments, the phase change material is a commercially available phase change material by PureTemp, such as: PureTemp 48, PureTemp 53, PureTemp 58, PureTemp 60, PureTemp 63, or PureTemp 68. In some embodiments, the phase change material is a commercially available phase change material by Climator, such as: Climsel C48, Climsel C58, or Climsel C70. In some embodiments, the phase change material is a commercially available phase change material by Rubitherm GmbH, such as: RT 50, RT 52, RT 55, RT 58, RT 60, RT 62, RT 65, RT 70 HC, RT 80 HC. RT 82, or RT 90 HC. In some embodiments, the phase change material is a commercially available phase change material by PlusICE, such as: S89, S83, S72, S70, S58, S50, A82, A70, A62, A60H, A60H, A58H, A58, A55, A53H, A53H, A52, or A50. In some embodiments, the phase change material is a commercially available phase change material by SAVENRG, such as: PCM-OM48P, PCM-OM53P, PCM-OM65P, or PCM-HS89P. In some embodiments, the phase change material is a commercially available phase change material by Microtek, such as: MPCM28D-IR or MPCM 56D. In some embodiments, the phase change material is a commercially available phase change material by Croda International Plc, such as Croda-Therm™ 53.

The embodiment depicted in FIG. 12 and described above include the remote-actuated expansion system 2107 as mating with the second block portion 2103'. In other embodiments, the remotely-actuated expansion system 2107 may instead mate with the first block portion 2103. In such embodiments, the second block portion 2103' may include the ratchet 2104, for example on the outside edges of the second block portion 2103', or along an inner channel of the second block portion 2103'. Activation of the remotely-actuated expansion system 2107 forces the second block portion 2103' away from the first block portion 2103 in a stepwise, incremental manner.

Figure 13:
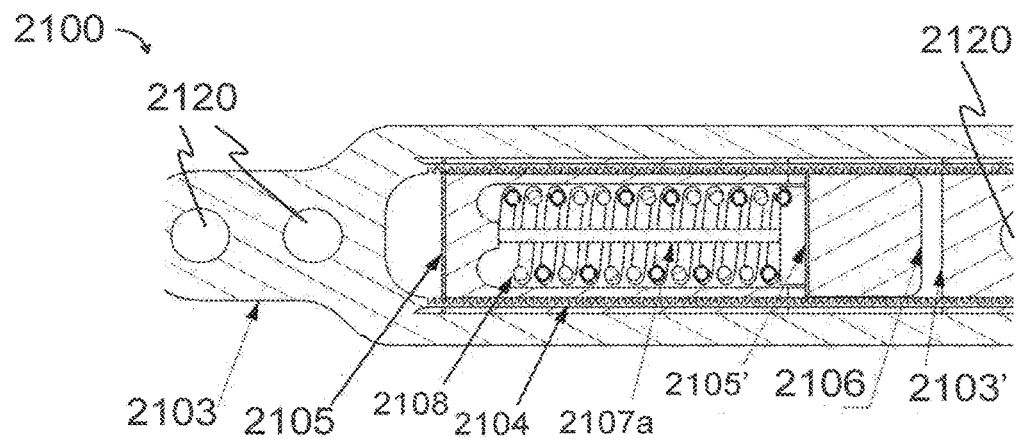
FIG. 13 shows a cross sectional top view of the remote-actuated bone distraction device of FIG. 12.
Figure 14:
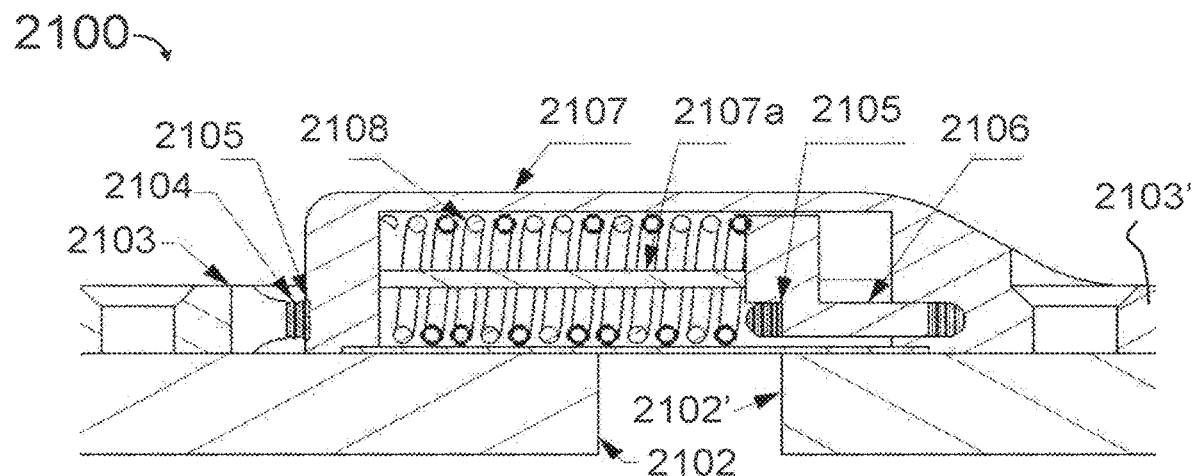
FIG. 14 shows a cross sectional side view of the remote-actuated bone distraction device of FIG. 12 anchored to two bone segments.

One embodiment of the remotely-actuated expansion system 2107 can be seen more clearly in FIGS. 13-14. In this embodiment, the remotely-actuated expansion system 2107 mates with the second block portion 2103' and includes a single length of shape memory alloy 2107a. A first pair of locking pawls 2105 and a second set of locking pawls 2105' each mate with the ratchet 2104 of the first block portion 2103. Upon input of a remote activation force, the shape memory alloy 2107a expands length-wise, forcing the floating element 2106 and the second block portion 2103' laterally away from the first block portion 2103. Once the lateral expansion from the shape memory alloy 2107a is sufficient to move the floating element 2106 and the second block portion 2103' a distance at least as large as the distance between successive teeth of the ratchet 2104, the ends of the second locking pawl 2105' will disengage from the initial teeth of the ratchet 2104 to engage the next adjacent set of teeth of the ratchet 2104. Potential energy (resistance) stored from concurrent deformation of a spring 2108 then draws the remainder of the remote-actuated expansion system 2107, including the associated first locking pawl 2105, towards the second bone segment 2102 as the shape memory alloy 2107a contracts.

In some embodiments, the remote actuation signal comprises heat, for example applied to the bone distraction device 2100 through wireless waves such as microwaves or radio waves. In some embodiments, the remote actuation signal does not require direct physical contact between the bone distraction device 2100 (or any component thereof) and the source of the remote actuation signal.

Figure 15:
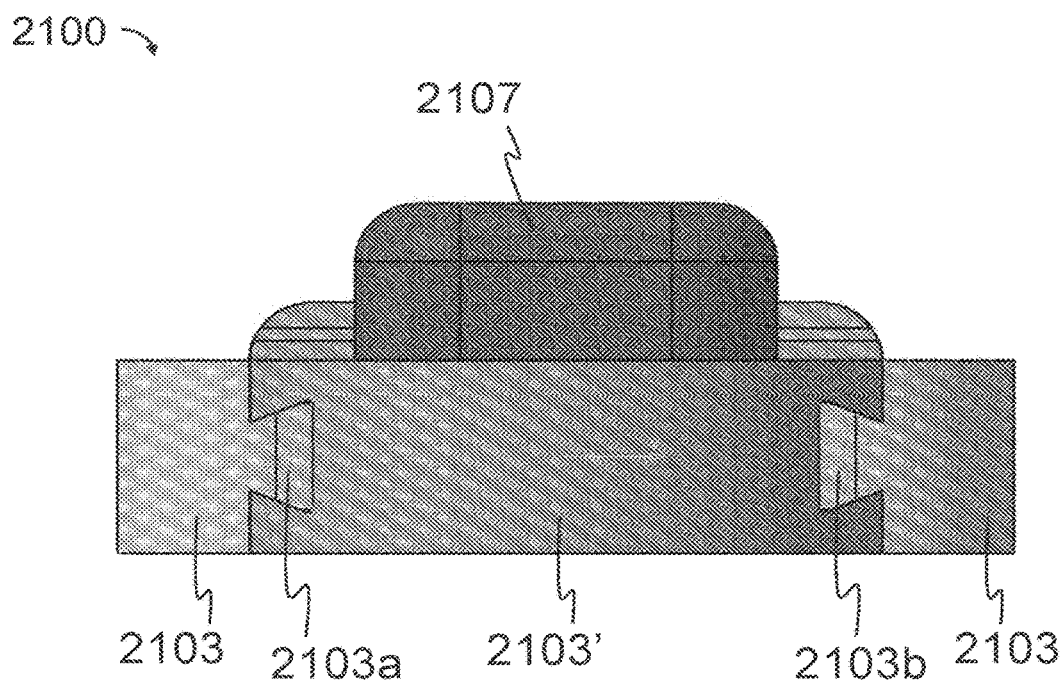
FIG. 15 shows a cross sectional end view of the remote-actuated bone distraction device of FIG. 12.

Referring now to FIG. 15, the second block portion 2103' may slidably mate with the first block portion 2103 along one or more rails 2103a,2103b. In some embodiments, such as that shown in FIG. 15, the one or more rails are a component of the first block portion 2103'. In such embodiments, the one or more rails 2103a,2103b may be in line with the ratchet 2104, such that the one or more rails 2103a,2103b serve as a positive stop that limits the expansion of the bone distraction device 2100 when the second block portion 2103' is advanced until the second locking pawl 2105' has reached the end of the ratchet 2104 and the beginning of the one or more rails 2103a,2103b.

In some embodiments, such as that shown in FIG. 15, the one or more rails 2103a,2103b have a cross sectional shape of a circle, an oval, a square, a rectangle, a pentagon, or a hexagon. In some embodiments, the one or more rails 2103a,2103b have a trapezoidal cross-sectional shape. Such a shape provides additional stability over rails 2103a,2103b that have a rectangular or square cross-sectional shape. For example, trapezoidal shaped rails 2103a,2103b such as those shown in FIG. 15 provide structural stability against undesired separation of the first block portion 2103 and the second block portion 2103' when the remote-actuated expansion system 2107 is actuated by the user.

Figure 16A:
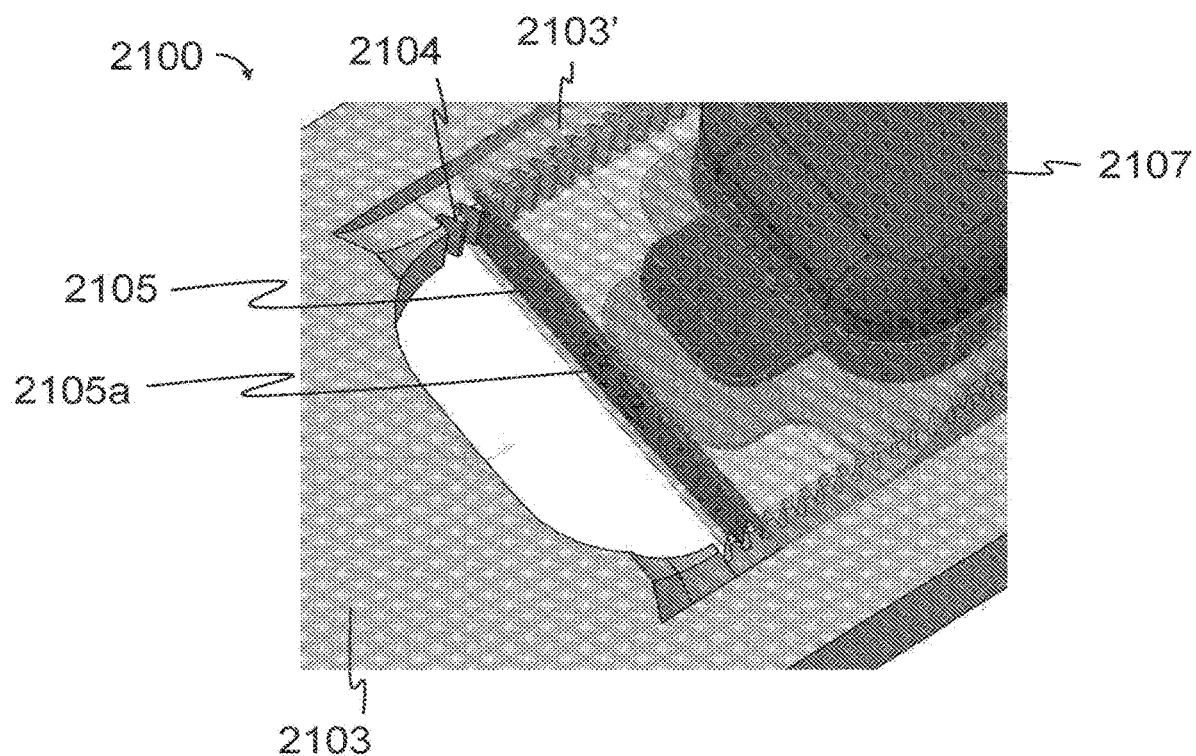
FIG. 16A shows a transparent perspective top view of a portion of the remote-actuated bone distraction device of FIG. 12.
Figure 16B:
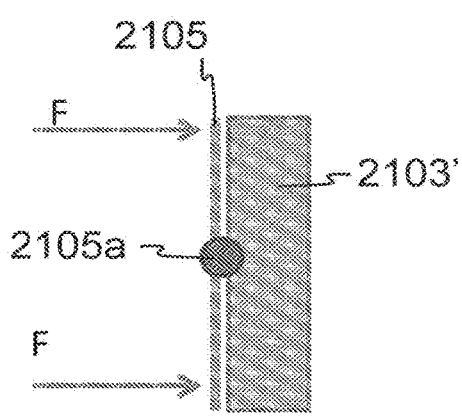
FIGS. 16B and 16C show forces applied to the first locking pawl at rest (FIG. 16B) and upon activation of the expansion system (FIG. 16C) of the remote-actuated bone distraction device of FIG. 12.
Figure 16C:
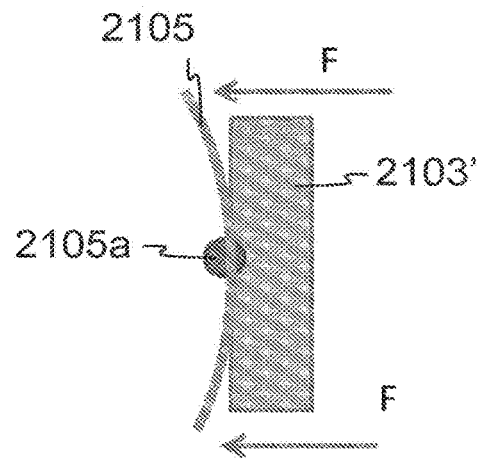

As shown in FIG. 16A, the first locking pawl 2105 may be attached to the end of the second block portion 2103' by one or more pawl anchors 2105a. The one or more pawl anchors 2105a are generally located at or near the midline of the first locking pawl 2105 so that the ends of the first locking pawl 2105 can flex away from the end of the second block portion 2103' as shown in FIG. 16C. This arrangement also prevents the second block portion 2103' from regressing toward the first block portion 2103 as shown in FIG. 16B.

In some embodiments, the bone distraction device 2100 further comprises at least one sensor (not shown). In general, the at least one sensor is in wireless communication with a data receiver (not shown) that converts the wireless signal from the at least one sensor into readable information about the growth of callus bone between the first bone segment 2102 and the second bone segment 2102' and/or about the position of the second block portion 2103' relative to the first block portion 2103.

In any embodiment disclosed herein, the first block portion 2103 and the second block portion 2103' may be made of any suitable bio-compatible material. In some embodiments, the first block portion 2103 and the second block portion 2103' comprise, consist essentially of, or consist of titanium, stainless steel, a titanium alloy, a non-titanium metallic alloy, a polymeric material, a plastic, a plastic composite, polyether ether ketone (PEEK), ceramic, and/or an elastic material.

In some embodiments, the bone distraction device 2100 further comprises a sensor 2110 for providing information about the position of one or more components of the bone distraction device 2100. The sensor 2110 may be any suitable sensor for determining a position of one or more components of the bone distraction device 2100. A plurality of sensors 2110 allows to determine position of one or more components of the bone distraction device 2100 and determine distraction Force, i.e. the force required to distract the bone portions. Additional sensors 2110 can determine extent of callus bone growth between the first bone portion 2102 and the second bone portion 2102'.

In some embodiments, the sensor 2110 is a position sensor associated with the expansion system 2207' and is in wireless communication with a receiver. In such embodiments, the position sensor 2110 transmits data about the position of the expansion system 2207', linked to the 2203'p fixed to the bone portion 2202' to the receiver.

In other embodiments, the sensor 2110 is a force sensor associated with the second block portion 2203'p and is in wireless communication with a receiver. In such embodiments, the force sensor 2110 transmits data about the force required to distract bone portions, taking into account the callus in formation between the bone portions and soft tissue of the bone block portion 2203'p to the receiver.

In other embodiments, the sensor 2110 is a vibration sensor associated with the floating elements 2107a & 2107b and is in wireless communication with a receiver. In such embodiments, the vibration sensor 2110 transmits data about the position of the floating elements 2107a & 2107b to the receiver.

In other embodiments, at least one sensor 2110 is an acoustic emission sensor associated with the floating elements 2107a & 2107b and is in wireless communication with a receiver. In such embodiments, the acoustic emission sensor 2110 transmits data about the position of the floating elements 2107a & 2107b to the receiver.

In some embodiments, the present disclosure provides a modular bone distraction device 2100 comprising: a first block portion 2103 including a pair of opposing rails 2103a, 2103b and a pair of opposing ratchet sections 2104; a second block portion 2103' that slidably mates with the first block portion 2103 and includes a first locking pawl 2105; and a translating expansion system 2107 for incrementally and slidably advancing the second block portion 2103' along the pair of opposing rails 2103a,2103b of the first block portion 2103, wherein the translating expansion system 2107 mates with the second block portion 2103' and with the pair of opposing ratchet sections 2104 to enable the second block portion 2103' to incrementally slide along the pair of opposing ratchet sections 2104, and wherein the translating expansion system 2107, upon activation, incrementally advances the second block portion 2103' along the pair of opposing ratchet sections 2104. In some embodiments, the first block portion 2103 further comprises at least one anchor hole 120 disposed through a thickness of the first block portion 2103. In some embodiments, the second block portion 2103' further comprises at least one anchor hole 120 disposed through a thickness of the second block portion 2103'. In some embodiments, the translating expansion system 2107 comprises a shape memory alloy 2107a for receiving a remote actuation signal from a user, a floating element 2106 for transferring input from the shape memory alloy 2107 into lateral motion, a second locking pawl 2105' associated with the floating element 2106 and with the pair of opposing ratchet sections 2104 of the first block portion 2103, a first energy storage element 2108 associated with the floating element 2106 for returning the floating element 2106 to its initial position after receiving input from the user, wherein the lateral motion of the floating element shape memory alloy 2107a does not induce rotational motion in the floating element 2107. In some embodiments, each activation of the translating expansion system 2107 advances the second block portion 2103' along the pair of opposing rails 2103a, 2103b by no more than about 0.25 mm. In some embodiments, each activation of the translating expansion system 2107 advances the second block portion 2103' along the pair of opposing rails 2103a,2103b by no more than about 0.2 mm. In some embodiments, each activation of the translating expansion system 2107 advances the second block portion 2103' along the pair of opposing rails 2103a,2103b by no more than about 0.15 mm. In some embodiments, each activation of the translating expansion system 2107 advances the second block portion 2103' along the pair of opposing rails 2103a,2103b by no more than about 0.1 mm. In some embodiments, the modular bone distraction device further comprises at least one sensor in wireless communication with a data receiving device and for determining growth of callus between a first bone section 2102 and a second bone section 2102'. In some embodiments, the at least one sensor comprises a first vibration sensor associated with the first locking pawl 2105 and a second vibration sensor 2109' associated with the second locking pawl 2105'. In some embodiments, the at least one sensor comprises a force sensor 1210 associated with the first locking pawl 2105. In some embodiments, the first block portion 2103 is for anchoring to a first bone section 2102, wherein the second block portion 3' is for anchoring to a second bone portion 2102', and wherein the first bone portion 2102 and the second bone portion 2102' are separated by a gap.

Figure 17:
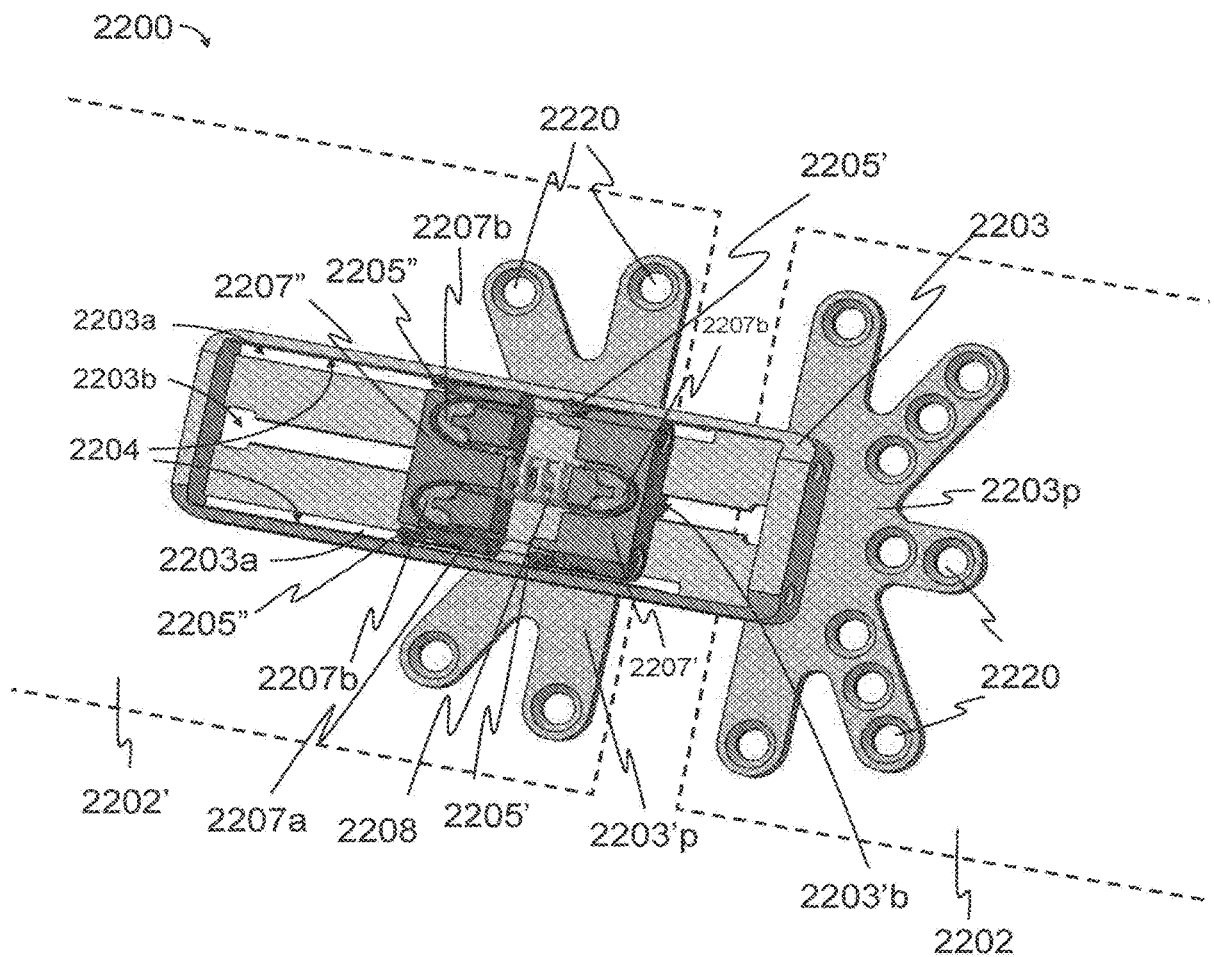
FIG. 17 shows a perspective view of a remote-actuated bone distraction device anchored to two bone segments according to another embodiment of the present disclosure.

Referring now to FIG. 17, a bone distraction device 2200 according to some embodiments of the present disclosure comprises a modular design that enables efficient and inexpensive preparation of individualized bone distraction devices to complement an individual subject's unique anatomical needs.

In general, a bone distraction device 2200 according to some embodiments of the present disclosure comprises a first block portion 2203 associated with a first anchor plate 2203p, and a second anchor plate 2203'p mated to a remote-actuated expansion system 2207 and slidably mated to the first block portion 2203.

The first anchor plate 2203p may feature any suitable shape consistent with the features and dimensions of the first bone portion 2202 using any suitable fastener such as a surgical screw (not shown). In some embodiments, the first anchor plate 2203p includes at least one anchor hole 2220.

In some embodiments, the first anchor plate 2203p includes at least two anchor holes 2220.

The second anchor plate 2203'p may feature any suitable shape consistent with the features and dimensions of the second bone portion 2202' using any suitable fastener such as a surgical screw (not shown). In some embodiments, the second anchor plate 2203'p includes at least one anchor hole 2220. In some embodiments, the second anchor plate 2203'p includes at least two anchor holes 2220.

The first block portion 2203 may further include a ratchet 2204 for enabling incremental expansion of the bone distraction device 2200 upon input from a user. In some embodiments, the ratchet 2204 includes a plurality of teeth that are spaced at a constant distance to provide even incremental expansion of the subcutaneous bone distraction device 2200 with each input by the user. In some embodiments, the spacing between the plurality of teeth is about 0.1 mm to 0.5 mm, for example about 0.1 mm, about 0.15 mm, about 0.2 mm, about 0.25 mm, about 0.3 mm, about 0.35 mm, about 0.4 mm, about 0.45 mm, or about 0.5 mm. In some embodiments, the spacing between the plurality of teeth is about 0.25 mm.

In other embodiments, the ratchet 2204 includes a plurality of teeth spaced at varying distances to enable incremental expansion of the bone distraction device 2200 with subsequent inputs by the user. For example and without limitation, in some embodiments the ratchet 4 may include teeth spaced at repeating intervals of about 0.25 mm, 0.25 mm, 0.25 mm, 0.5 mm, 0.25 mm, 0.25 mm, 0.25 mm, 0.5 mm, etc. In such embodiments, the larger interval enables the user to expand the bone distraction device 2200 just once before an overnight rest period without being forced to wake before dawn to provide an additional input to expand the bone distraction device 2200.

The remote-actuated expansion system 2207 in some embodiments may comprise a first floating element 2207' and a second floating element 2207'' expandably associated with the first floating element 2207' by a shape memory alloy 2207a and a spring 2208. The first floating element 2207' may include a first locking pawl 2205' (or a first pair of locking pawls 2205') that engages with the ratchet 2204 to provide incremental expansion of the bone distraction device 2200 along the length of the first block portion 2203. In some embodiments, the first locking pawl 2205' comprises a flexible tab that is forced against the ratchet 2204 by a spring force. The first locking pawl 2205' enables the first floating element 2207' to slide in one direction against the first block portion 2203, but prevents the first floating element 2207' from sliding in the opposite direction against the first block portion 2203. The second floating element 2207'' may include a second locking pawl 2205'' (or a second pair of locking pawls 2205'') that engages with the ratchet 2204 to provide incremental advancement of the second floating element 2207'' along the length of the first block portion 2203. In some embodiments, the second locking pawl 2205'' comprises a flexible tab that is forced against the ratchet 2204 by a spring force. The second locking pawl 2205'' enables the second floating element 2207'' to slide in one direction against the first block portion 2203, but prevents the second floating element 2207'' from sliding in the opposite direction against the first block portion 2203.

In some embodiments, the remotely-actuated expansion system 2207 includes a shape memory alloy 2207a that is configured to force the second anchor plate 2207p to slide in a single direction along the ratchet 2204 upon activation by the user. In some embodiments, such as that shown in FIG. 17, the remotely-activated expansion mechanism 2207 includes a shape memory alloy 2207a and a spring 2208. In some embodiments, the first floating element 2207' and the second floating element 2203b are expandably associated with each other by more than one lengths of shape memory alloy 2207a, such as two lengths of shape memory alloy 2207a, three lengths of shape memory alloy 2207a, four lengths of shape memory alloy 2207a, five lengths of shape memory alloy 2207a, six lengths of shape memory alloy 2207a, or more than six lengths of shape memory alloy 2207a. In some embodiments, more than one length of shape memory alloy 2207a between the first subunit 2207' and the second subunit 2203b represent a continuous piece of shape memory alloy 2207a. In some embodiments, all of the lengths of shape memory alloy 2207a between the first subunit 2207' and the second subunit 2203b represent a continuous piece of shape memory alloy 2207a. For example and without limitation, the embodiment shown in FIG. 17 includes four lengths of shape memory alloy 2207a expandably connecting the first floating element 2207' and the second floating element 2203b, and each of the four lengths of the shape memory alloy 2207a represent a continuous piece of shape memory alloy 2207a that is bent at a number of apices 2207b that is one less (three in this embodiment) than the number of lengths of shape memory alloy 2207a (four in this embodiment).

Upon input of a remote activation force, the shape memory alloy 2207a expands length-wise, forcing the first floating element 2207' laterally away from the second bone segment 2202'. Once the lateral expansion from the shape memory alloy 2207a is sufficient to move the first floating element 2207' a distance at least as large as the distance between successive teeth of the ratchet 2204, the ends of the first locking pawl 2205' will disengage from the initial teeth of the ratchet 2204 to engage the next adjacent set of teeth of the ratchet 2204. Potential energy (resistance) stored from concurrent deformation of the spring 2208 then draws the second floating element 2203b, including the associated second locking pawl 2205'', towards the first bone segment 2202 as the shape memory alloy 2207a contracts.

In some embodiments, first block portion 2203 includes slots or grooves 2203a,2203b that sildeably mate with the first floating element 2207' and the second floating element 2207'' and guide proper alignment of the first floating element 2207' and the second floating element 2207'' along the length of the first block portion 2203. In some embodiments, the first floating element 2207' includes a first guide tab (not shown) that slidably mates with the first slot or groove 2203a. In some embodiments, the first floating element 2207' includes a second guide tab 2203'b that slidably mates with the second slot or groove 2203b.

In some embodiments, a first slot or groove 2203a is disposed at or near the ratchet 2204 side(s) of the first block portion 2203. In some embodiments, a second slot or groove 2203b is disposed at or near the midline of the first block portion 2203. In some embodiments, a first slot or groove 2203a is disposed at or near the ratchet 2204 side(s) of the first block portion 2203 and a second slot or groove 2203b is disposed at or near the midline of the first block portion 2203. One or more of the first slot or groove 2203a and/or the second slot or groove 2203b may have a length that is less than the full length of the first block portion 2203 to provide a positive stop for the first subunit 2207'. In such embodiments, the length of the first slot or groove 2203a and/or the second slot or groove 2203b defines a maximum extent of distraction possible through use of the bone distraction device 2200.

In some embodiments, the present disclosure provides a modular actuator 2207. The modular actuator 2207 can be mated with customizable anchor plates. In some embodiments, the modular actuator 2207 comprises: a first floating element 2207' comprising at least one locking pawl 2205': a second floating element 2207" comprising at least one locking pawl 2205 and separated from the first floating element 2207' by a baseline distance: at least one length of shape memory alloy 2207a connected to the first floating element 2207' and to the second floating element 2207"; and a spring 2208 connected to the first floating element 2207' and to the second floating element 2207", activation of the at least one length of shape memory alloy (2207a) forces the first floating element (2207') to come closer to the second floating element (2207") by a reduced distance that is smaller than the baseline distance, compressing the spring (2208) and wherein the released energy of the spring (2208) causes the second floating element (2207") to move away the first floating element (2207') in order to obtain again the baseline distance for a next cycle. In some embodiments, the first floating element 2207' includes two locking pawls 2205', and wherein the second floating element 2207" includes two locking pawls 2205. In some embodiments, the modular actuator 2207 comprises at least two lengths of the shape memory alloy 2207a. In some embodiments, the modular actuator 2207 comprises at least three lengths of the shape memory alloy 2207a. In some embodiments, the modular actuator 2207 comprises at least four lengths of the shape memory alloy 2207a. In some embodiments, the locking pawls 2205,2205' engage with one or more ratchet lengths of the bone distraction device for enabling incremental step-wise motion of the modular actuator along the one or more ratchet lengths. In some embodiments, the modular actuator 2207 further comprises a phase change material in thermal communication with the shape memory alloy 2207a for absorbing heat liberated by the shape memory alloy 2207a after activation of the shape memory alloy 2207a. In some embodiments, the shape memory alloy 2207a does not cause rotational movement of the second floating element 2207" relative to the first floating element 2207'.

Figures 18A, 18B:
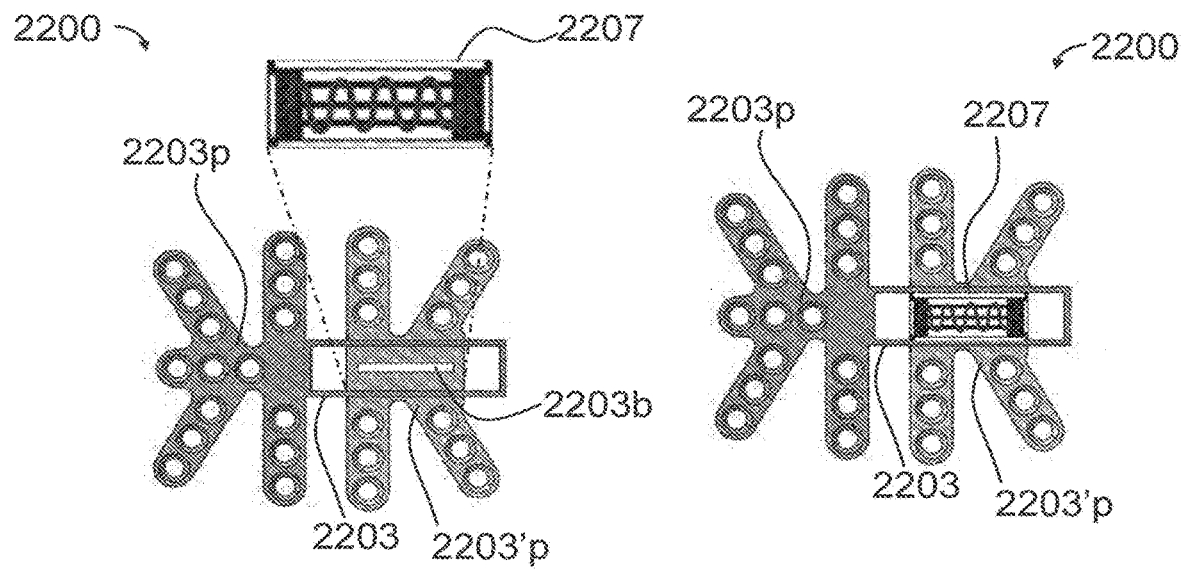
FIG. 18A shows a schematic view of the remote-actuated bone distraction device of FIG. 17 including customizable anchor plates and a removable actuating system.
FIG. 18B shows a schematic view of the assembled remote-actuated bone distraction device of FIG. 18A.

Advantages of the modular design of bone distraction devices according to the present disclosure are easily seen in FIGS. 18A-18B. In some embodiments, the remote-actuated expansion system 2207 is a modular unit that mates with a slot or groove 2203b of the second block portion 2203'p. The locking pawls 2205',2205" engage with the ratchets 2204 of the first block portion 2203. The modular design of the remote-actuated expansion system 2207 enables customization of the first anchor plate 2207'p and the second anchor plate 2207"p while using the same modular actuator 2207

In some embodiments, the remote actuation signal comprises heat, for example applied to the bone distraction device 2200 through wireless waves such as microwaves or radio waves. In some embodiments, the remote actuation signal does not require direct physical contact between the bone distraction device 2200 (or any component thereof) and the source of the remote actuation signal.

In some embodiments, the bone distraction device 2200 further comprises at least one sensor (not shown). In general, the at least one sensor is in wireless communication with a data receiver (not shown) that converts the wireless signal from the at least one sensor into readable information about the growth of callus bone between the first bone segment 2202 and the second bone segment 2202' and/or about the position of the second block portion 2203'p,2203b relative to the first block portion 2203,2203p, and/or about the force required to distract the second block portion 2203'p relative to the first block portion 2203p.

In any embodiment disclosed herein, the first block portion 2203 and the second anchor plate 2203p may be made of any suitable bio-compatible material. In some embodiments, the first block portion 2203 and the second anchor plate 2203'p comprise, consist essentially of, or consist of titanium, stainless steel, a titanium alloy, a non-titanium metallic alloy, a polymeric material, a plastic, a plastic composite, polyether ether ketone (PEEK), ceramic, and/or an elastic material.

In some embodiments, the bone distraction device 2200 further comprises a sensor for providing information about the position of one or more components of the bone distraction device 2200. The sensor may be any suitable sensor for determining a position of one or more components of the bone distraction device 2200, and/or for determining extent of callus bone growth between the first bone portion 2202 and the second bone portion 2202' and/or for determining the force to distract the first bone portion 2202 and the second bone portion 2202'.

In some embodiments, the sensor is a position sensor associated with the floating element 2107b/2107c/2207'/2207" and is in wireless communication with a receiver. In such embodiments, the position sensor transmits data about the position of the floating element 2107b/2107c/2207'/2207" to the receiver.

In other embodiments, the sensor is a force sensor associated with the floating element 2107b/2107c/2207'/2207" and is in wireless communication with a receiver. In such embodiments, the force sensor transmits data about the position of the floating element 2107b/2107c/2207'/2207" to the receiver.

In other embodiments, the sensor is a vibration sensor associated with the floating element 2107b/2107c/2207'/2207" and is in wireless communication with a receiver. In such embodiments, the vibration sensor transmits data about the position of the floating element 2107b/2107c/2207'/2207" to the receiver.

In other embodiments, the sensor is an acoustic emission sensor associated with the floating element 2107b/2107c/2207'/2207" and is in wireless communication with a receiver. In such embodiments, the acoustic emission sensor transmits data about the position of the floating element 2107b/2107c/2207'/2207" to the receiver.

In some embodiments, the present disclosure provides a modular bone distraction device (2200) comprising: a first block portion (2203) including at least one slot or groove (2203a,2203b) parallel to a length of the first block portion (2203) and pair of opposing ratchet sections (2204) along the length of the first block portion (2203); a second anchor plate (2203'p) that slidably mates with the first block portion (2203); and a remote-activated expansion system (2207) for incrementally advancing the second anchor plate (2203'p) along the pair of opposing ratchet sections (2204), wherein the modulate remote-activated expansion system (2207) comprises a first floating element (2207') expandably associated with a second floating element (2207") by a shape memory alloy (2207a) and a spring (2208) includes a first locking pawl (2205') and an expansion system (2207) for incrementally and slidably advancing the second block portion (2207'/2207") along the at least one slot or groove (2203a,2203b) of the first block portion (2203). In some embodiments, the first floating element (2207') includes a first pair of locking pawls (2205') that engage with the pair of opposing ratchet sections (2204) to enable the first floating element (2207') to advance along the pair of opposing ratchet sections (2204) in a first direction but not in a second, opposite direction, and wherein the second floating element (2207") includes a second pair of locking pawls (2205") that engage with the pair of opposing ratchet sections (2204) to enable the second floating element (2207") to advance along the pair of opposing ratchet sections (2204) in the first direction but not in the second, opposite direction. In some embodiments, the first block portion (2203) further comprises a first anchor plate (2203p) including at least one anchor hole (2220) disposed through a thickness of the first anchor plate (2203p) for anchoring the first anchor plate (2203p) to a first bone segment (2202), and wherein the second anchor plate (2203'p) at least one anchor hole (2220) disposed through a thickness of the second anchor plate (2203'p) for anchoring the second anchor plate (2203'p) to a first bone segment (2202). In some embodiments, the expansion system (2207) comprises a shape memory alloy (2207a) for advancing the second anchor plate (2203'p) along the pair of opposing ratchet sections (2204) upon receiving a remote actuation signal from a user, and a spring (2208) for contracting the second block portion (2207'/2207") after the expansion of the second block portion (2207/2207") is complete. In some embodiments, each activation of the expansion system (2207) advances the second anchor plate (2203'p) along the first slot or groove (2203a) and/or along the second slot or groove (2203b) by no more than about 0.25 mm. In some embodiments, each activation of the expansion system (2207) advances the second anchor plate (2203'p) along the first slot or groove (2203a) and/or along the second slot or groove (2203b) by no more than about 0.2 mm. In some embodiments, each activation of the expansion system (2207) advances the second anchor plate (2203'p) along the first slot or groove (2203a) and/or along the second slot or groove (2203b) by no more than about 0.15 mm. In some embodiments, each activation of the expansion system (2207) advances the second anchor plate (2203'p) along the first slot or groove (2203a) and/or along the second slot or groove (2203b) by no more than about 0.1 mm. In some embodiments, the modular bone distraction device further comprises at least one sensor in wireless communication with a data receiving device and for determining growth of callus between a first bone section (2202) and a second bone section (2202"). In some embodiments, the at least one sensor comprises a first vibration sensor associated with the first locking pawl (2205) and a second vibration sensor (2209') associated with the second locking pawl (2205').

Figures 19A, 19B:
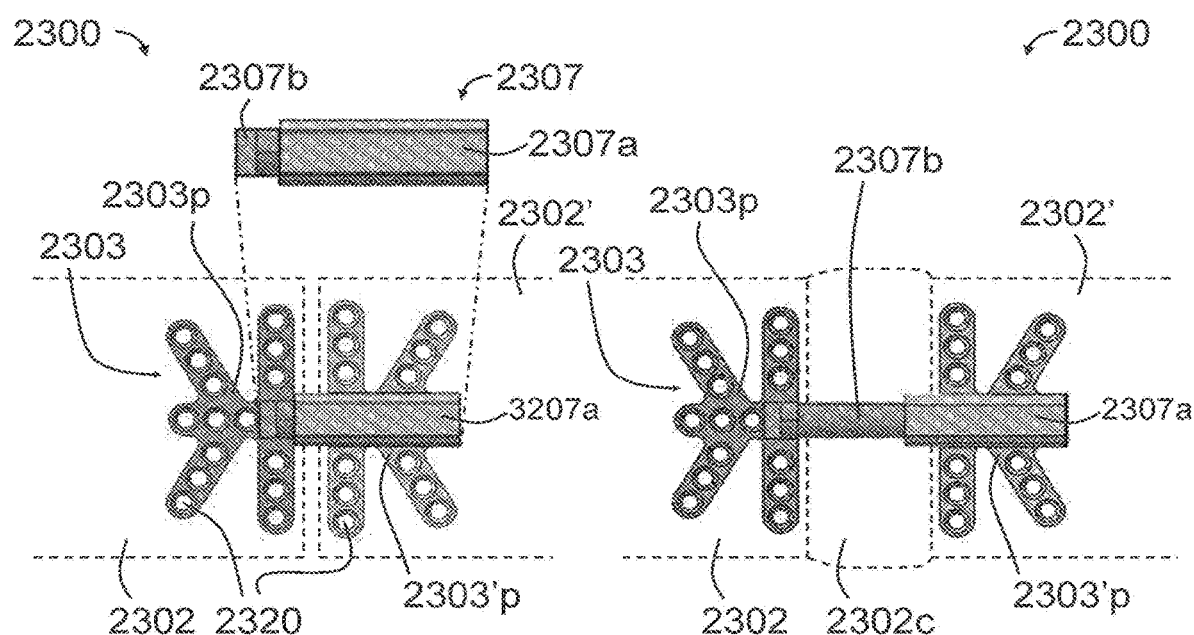
FIG. 19A shows a schematic view of a remote-actuated bone distraction device including customizable anchor plates and a removable actuating system according to another embodiment of the present disclosure.
FIG. 19B shows a schematic view of the remote-actuated bone distraction device of FIG. 19A in use, and after a series of activating events has separated two bone segments to induce growth of callus bone therebetween.

Referring now to FIGS. 19A-19B, a modular remote-activated bone distraction device 2300 according to one embodiment of the present disclosure comprises a first block portion including a first anchor plate 2303p, a second anchor plate 2303'p, and a modular remote-activated expansion system 2307 that mates with the second anchor plate 2303'p and the first block portion 2303.

The modular remote-activated expansion system 2307 includes a first element 2307a including a lead screw, and a second element 2307b including a motor and a gearbox in mechanical communication with the lead screw.

In operation, the first anchor plate 2303p is anchored to a first bone segment 2302 using an anchor (not shown) through one or more anchor holes 2320, and the second anchor plate 2303'p is anchored to a second bone segment 2302' using an anchor (not shown) through one or more anchor holes 2320.

Referring to FIGS. 20A-20D, the a modular remote-activated bone distraction device 2400 according to one embodiment of the present disclosure comprises a first block portion including a first anchor plate 2403p, a second anchor plate 2403'p, and a modular remote-activated expansion system 2407. The modular remote-activated expansion system 2407 includes a first element 2407a including a lead screw, and a second element 2407b including a motor and a gearbox in mechanical communication with the lead screw.

Figure 20A:
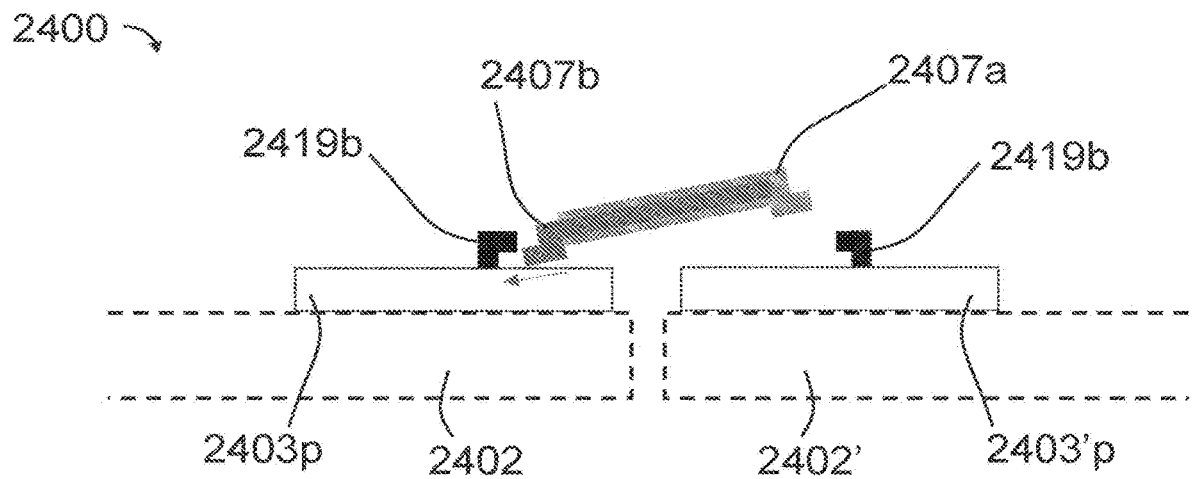
FIGS. 20A-20D show sequential mating of a modular activator with anchor plates associated with two separated bone segments.
Figure 20B:
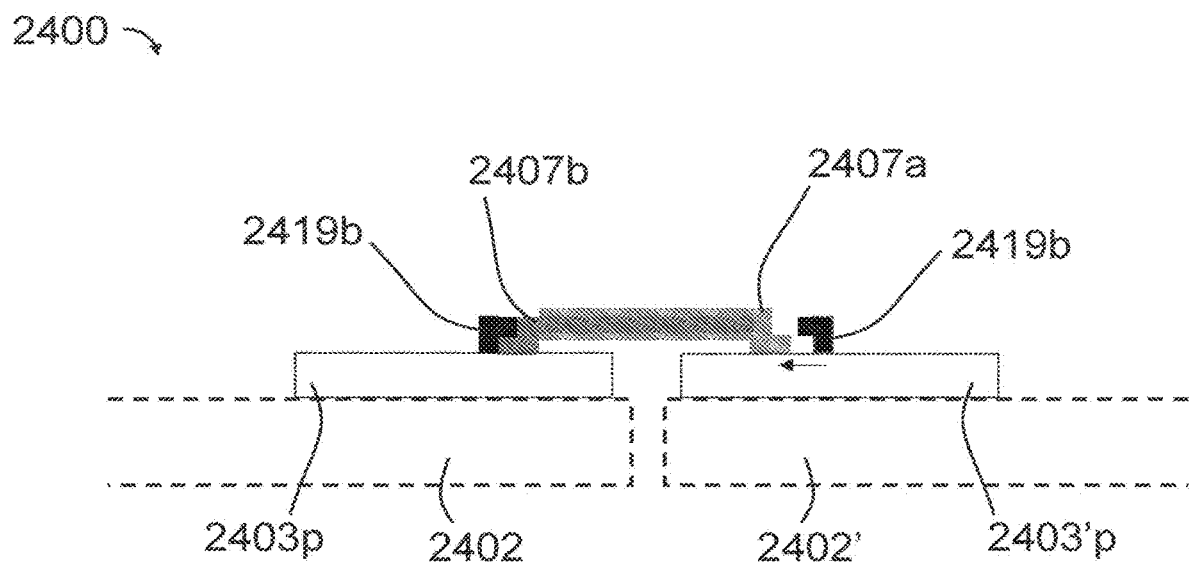
Figure 20C:
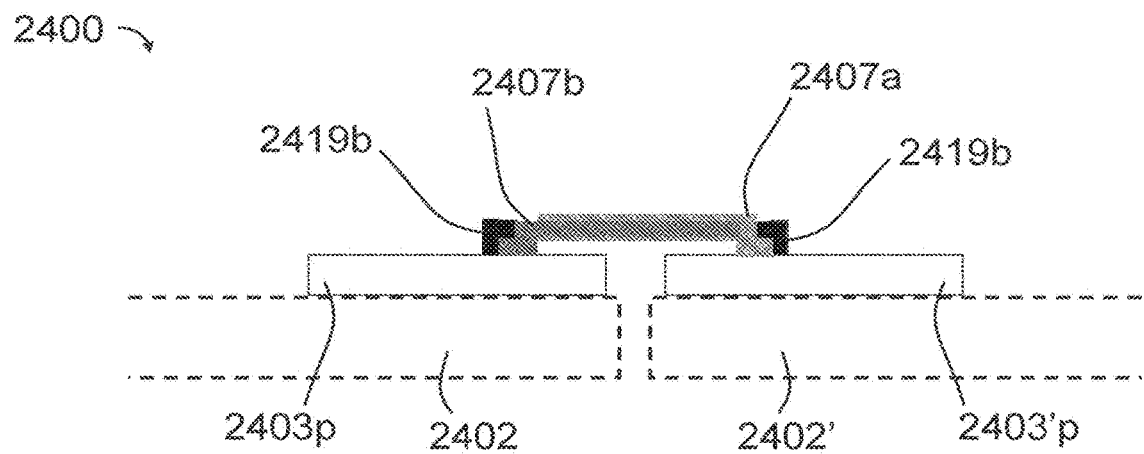
Figure 20D:
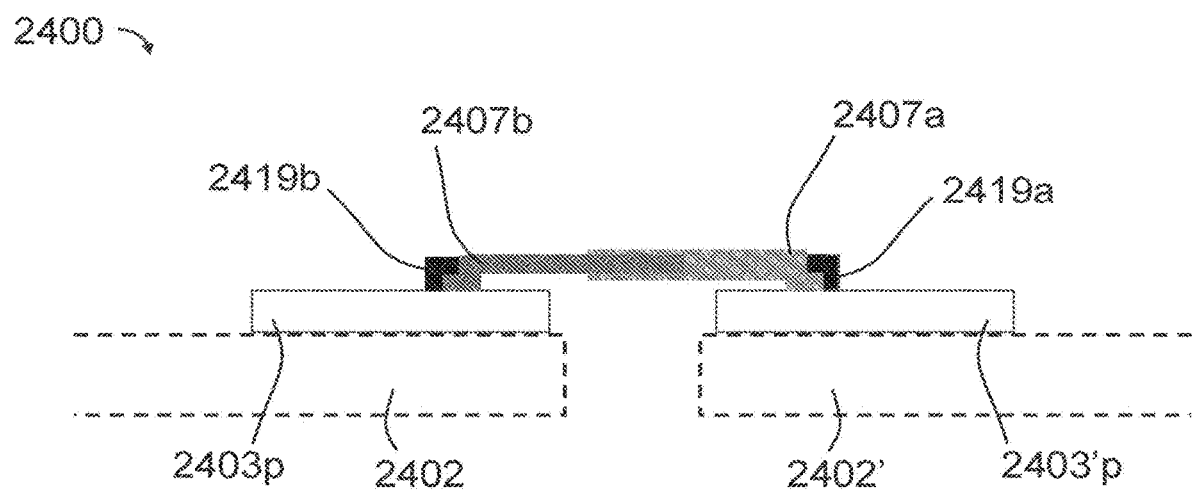
Figure 21A:
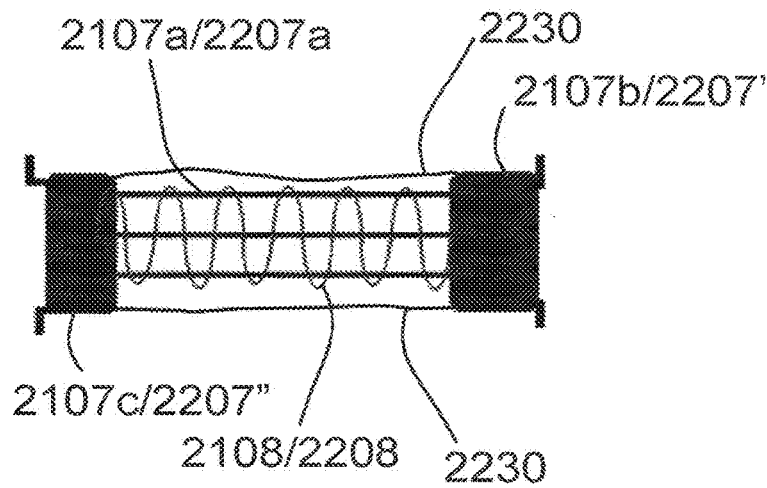
FIG. 21A shows an implantable actuator including an insulating membrane surrounding the shape memory alloy.
Figure 21B:
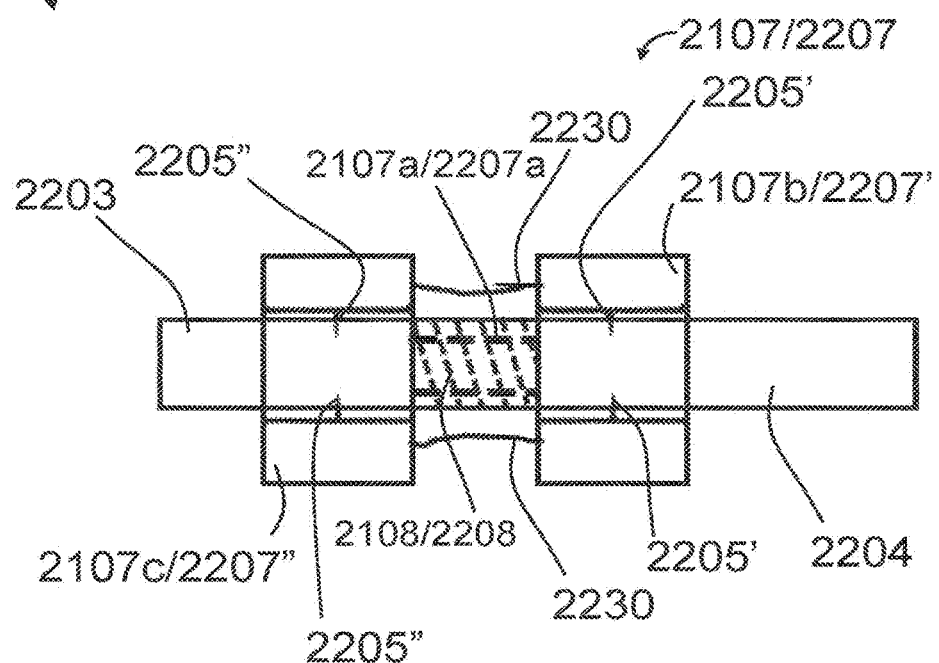
FIG. 21B shows a top view of an implantable bone distraction device including the implantable actuator of FIG. 21A.
Figure 21C:
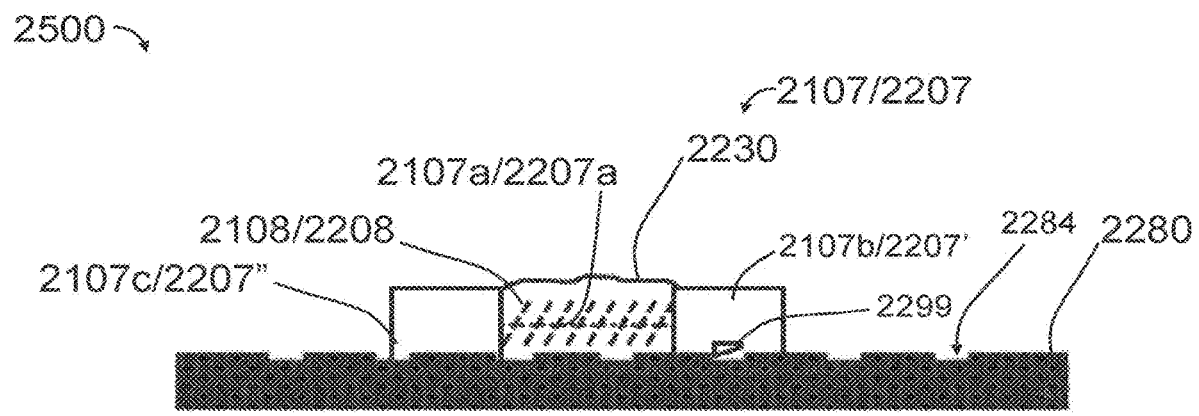
FIG. 21C shows a side view of the implantable bone distraction device of FIG. 21B.
Figure 21D:
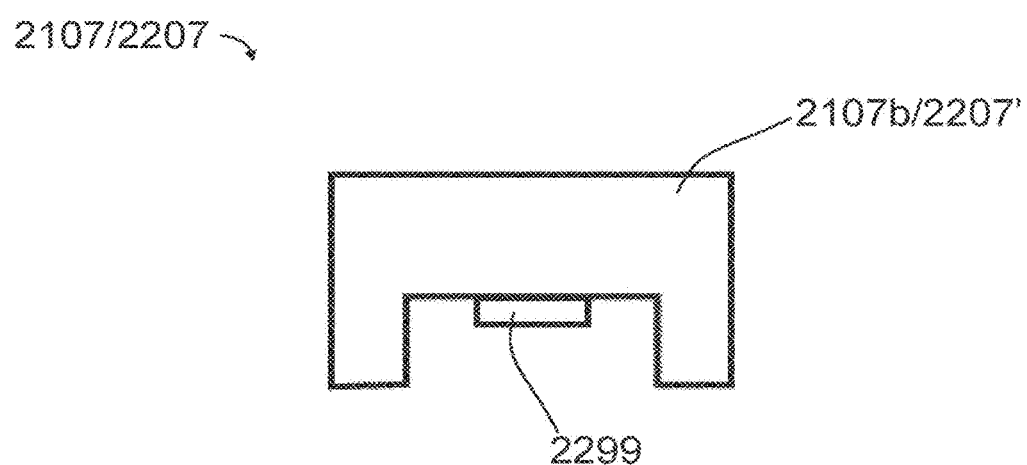
FIG. 21D shows a front view of the implantable actuator of FIG. 21A.

In operation, the first anchor plate 2407p is anchored to a first bone segment 2402 using an anchor (not shown), and the second anchor plate 2403'p is anchored to a second bone segment 2402' using an anchor (not shown). The second element 407b is mated with a first binding element 2419b of the first anchor plate 2403p, as shown in FIG. 20A. Thereafter, the first element 2407a is mated with a second binding element 2419a of the second anchor plate 2403'p. In some embodiments, the second binding element 2419b is slid into a mating relationship with the first element 2407a, for example as shown in FIG. 20B. Actuation of the modular remote-actuated expansion system 2407 forces the second anchor plate 2407'p away from the first anchor plate 2407p, as shown in FIGS. 20C-20D.

Referring now to FIGS. 21A-21D, a bone distraction device 2500 consistent with the present disclosure may include an implantable actuator 2107/2207 that includes a flexible membrane 2230 for shielding the shape memory alloy 2107a/2207a and the spring 2108/2208 from contacting bodily fluids and tissue after implantation. In some embodiments, the bone distraction device 2500 includes a first floating element 2107b/2207' that comprises a locking wedge 2299 not in alignment with locking pawls 2205'. In such embodiments, the locking wedge 2299 may be aligned with a series of recesses 2284 in the track 2280, such that the locking wedge 2299 mates with the next successive recess 2284 as the first floating element 2107b/2207' advances along the track 2280 in response to motive force from the implantable actuator 2107/2207. Although not required in all embodiments, the presence of the locking wedge 2299 in bone distraction devices 2100/2200/2300/2400/2500/2600 of the present disclosure further reduces the risk that the first floating element 2107b/2207' retracts, or fails to advance, along the track 2280 in response to motive force from the implantable actuator 2107/2207. Such bone distraction devices 2500 may otherwise be consistent with any bone distraction device 2100/2200/2300/2400/2600 disclosed herein.

Figure 22:
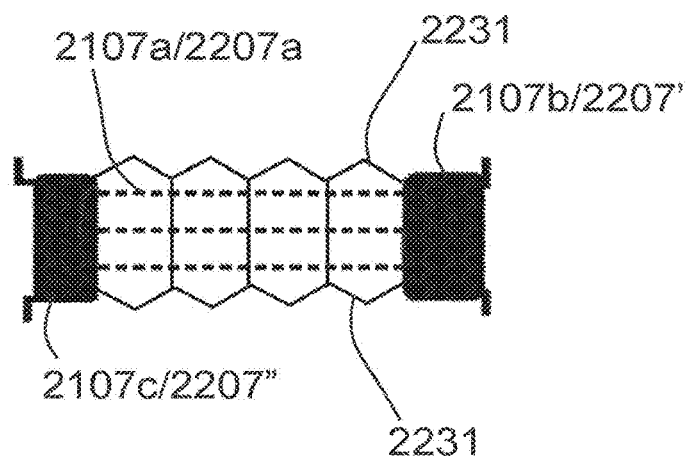
FIG. 22 shows an implantable actuator including an insulating and elastic membrane surrounding the shape memory alloy.

As shown in FIG. 22, a bone distraction device 2100/2200/2300/2400/2600 consistent with the present disclosure may include an implantable actuator 2107/2207 that includes a bellowed membrane 2231 for shielding the shape memory alloy 2107a/2207a and the optional spring 2108/2208 from contacting bodily fluids and tissue after implantation. Such bone distraction devices 2100/2200/2300/2400/2600 may otherwise be consistent with any bone distraction device 2100/2200/2300/2400/2600 disclosed herein. In some embodiments, the implantable actuator 2107/2207 in these bone distraction devices 2100/2200/2300/2400/2600 does not include the optional spring 2108/2208; in such embodiments the bellowed configuration of the bellowed membrane 2231 provides a sufficient spring force to separate the first floating element 2107b/2207' from the second floating element 2107c/2207" after contraction by the shape memory alloy 2107a/2207a.

Figure 23:
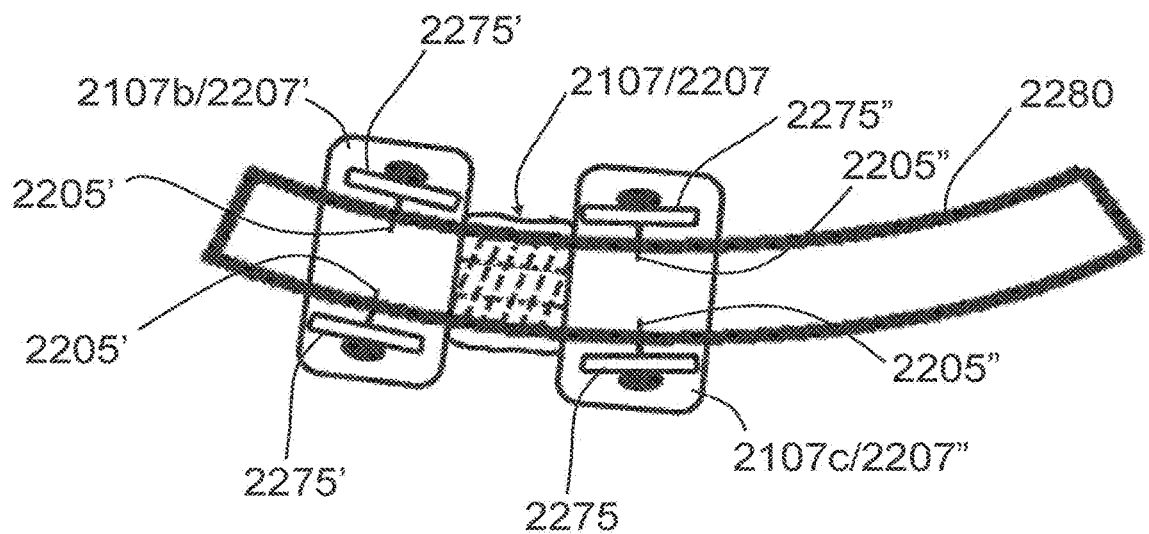
FIG. 23 shows an implantable actuator capable of distracting bone segments along a non-linear (e.g., curved) path The figures depict various embodiments of this disclosure for purposes of illustration only. One skilled in the art will readily recognize from the following discussion that alternative embodiments of the structures and methods illustrated herein may be employed without departing from the principles of embodiments described herein.

Referring now to FIG. 23, a bone distraction device 2600 consistent with the present disclosure suitable for distracting bone segments along a non-linear (e.g., curved) path may include a first floating element 2107b/2207' and a second floating element 2107c/2207" connected by an implantable actuator 2107/2207. The first floating element 2107b/2207' may include one or more locking pawls 2205', each secured to the first floating element 2107b/2207' by a flexible joint 2275' (e.g., a ball-and-socket joint) that enables the locking pawl(s) 2205' to engage a non-linear (e.g., curved) track 2280. The second floating element 2107c/2207" may include one or more locking pawls 2205", each secured to the second floating element 2107c/2207" by a flexible joint 2275" (e.g., a ball-and-socket joint) that enables the locking pawl(s) 2205" to engage a non-linear (e.g., curved) track 2280. The flexible joints 2275'/2275" enable the bone distraction device 2600 to follow the non-linear path of the non-linear track 2280 while still employing a substantially linear locomotion force from the implantable actuator 2107/2207.

In some embodiments, the present disclosure provides an implantable actuator for a bone distraction device, the implantable actuator comprising: a first floating element (2207') comprising at least one locking pawl (2205'): a second floating element (2207") comprising at least one locking pawl (2205) and separated from the first floating element (2207') by a baseline distance: at least one length of shape memory alloy (2207a) connected to the first floating element (2207') and to the second floating element (2207"): an insulating membrane (230) surrounding the shape memory alloy (2207a); and at least one spring (2208) connected to the first floating element (2207') and to the second floating element (2207"), wherein activation of the at least one length of shape memory alloy (2207a) compresses the spring (2208) and forces the first floating element (2207') to move towards to the second floating element (2207") such that the first floating element (2207') and the second floating element (2207") are separated by a reduced distance that is smaller than the baseline distance; and wherein a subsequent release of energy from decompression of the spring (2208) causes the second floating element (2207") to move away the first floating element (2207') such that the first floating element (2207') and the second floating element (2207") are separated by the baseline distance. In some embodiments, the subsequent release of energy occurs without a second activation of the at least one length of shape memory alloy (2207a).

In some embodiments, the present disclosure provides an implantable actuator for a bone distraction device, the implantable actuator comprising: a first floating element (2207') comprising at least one locking pawl (2205'): a second floating element (2207") comprising at least one locking pawl (2205) and separated from the first floating element (2207') by a baseline distance: at least one length of shape memory alloy (2207a) connected to the first floating element (2207') and to the second floating element (2207"): an insulating and elastic membrane (231) surrounding the shape memory alloy (2207a), wherein activation of the at least one length of shape memory alloy (2207a) compresses the insulating and elastic membrane (231), forcing the first floating element (2207') to move closer to the second floating element (2207") such that the first floating element (2207') and the second floating element (2207") are separated by a reduced distance that is smaller than the baseline distance, and wherein a subsequent release of energy from the compressed insulating and elastic membrane (231) causes the second floating element (2207") to move away from the first floating element (2207') such that the first floating element (2207') and the second floating element (2207") are separated by the baseline distance.

4. Methods of Lengthening Bone Using Modular Bone Distraction Devices

Remotely-activated bone distraction devices 2100,2200 consistent with the present disclosure are useful for lengthening a bone of a subject, such as a human subject.

Generally, methods of lengthening bone disclosed herein comprise implanting a bone distraction device 2100,2200 to two adjacent bone segments and completely under the skin of a subject, and periodically applying an actuating force to the bone distraction device 2100,2200 to expand the bone distraction device 2100,2200 in a single direction. In some embodiments, the method further comprises creating a gap in a bone to form two adjacent bone segments (e.g., osteotomy or corticotomy) before implanting the bone distraction device 2100,2200.

In some embodiments, the bone distraction device 2100, 2200 comprises a first block portion 2103,2203 and a second block portion 2103',2207'/2207" that is slidably mated to the first block portion 2103,2203. The method of lengthening a bone using such a bone distraction device 2100,2200 comprises anchoring the first block portion 2103,2203 to a first segment of bone 2102,2202, and anchoring the second block portion 2103',2207'/2207" to a second segment of bone 2102',2202'. In some embodiments, the first block portion 2103,2203 is anchored to the first bone segment 2102,2202, and the second block portion 2103',2207'/2207" is thereafter slidably mated to the first block portion 2103,2203 before the second block portion 2103',2207'/2207" is anchored to the second bone segment 2102',2202'. In another embodiment, the second block portion 2103',2207'/2207" is anchored to the second bone segment 2102',2202', and the first block portion 2103,2203 is thereafter slidably mated to the second block portion 2103',2207'/2207" before the first block portion 2103,2203 is anchored to the first bone segment 2102,2202. In another embodiment, the first block portion 2103,2203 and the second block portion 2103',2207'/2207" are slidably mated together before one block portion (e.g., the first block portion 2103, 2203) is anchored to one bone segment (e.g., the first bone segment 2102,2202) before the other block portion (e.g., the second block portion 2103',2207'/2207") is anchored to the other bone segment (e.g., the second bone segment 2102',2202').

Once anchored to the two adjacent bone segments, the bone distraction device 2100,2200 is actuated in a series of repeated cycles. In general, each cycle comprises steps of: causing the bone distraction device 2100,2200 to expand in a single direction substantially parallel to the long dimension of the bone segments, and waiting for callus bone to form between the two adjacent bone segments.

Causing the bone distraction device 2100,2200 to expand is generally accomplished by remotely applying an actuating force to the expansion system 2107,2207 of the bone distraction device 2100,2200. For example, a remote source of heat wave energy applied to the 2107,2207 causes a shape metal alloy 2107a,2207a to expand, which in turn forces the second block portion 2103',2207'/2207" to slide laterally away from the first block portion 2103,2203 by a predetermined distance (e.g., 0.25 mm).

In some embodiments, such as embodiments in which the bone distraction device 2100,2200 additionally includes one or more sensors, the step of waiting for callus bone to grow between the first bone segment 2102,2202 and the second bone segment 2102',2202' may comprise obtaining data from the sensor about callus bone growth progress and/or the degree of expansion of the second block portion 2103', 2207'/2207" from the first block portion 2103,2203 before causing the subcutaneous bone distraction device 2100,2200 to expand in a subsequent cycle. In some embodiments, a subsequent step of actuating the bone distraction device is prevented by the bone distraction device or by the remote actuating device if data from the one or more sensors indicates that callus bone formation has not reached a desired level.

Once the bone has been lengthened to the desired extent, the method may optionally include removing the bone distraction device 2100,2200 from the subject.

The methods disclosed herein may be used to distract any suitable bone, but are particularly suited for distracting bones in anatomical areas of a subject that are inconvenient for accessing by physical actuating tools (e.g., torsion drivers or wrenches) and/or require individualized design to accommodate unique bone features of an individual subject.

In one embodiment, the present disclosure provides a method of lengthening a bone in a subject, the method comprising: anchoring a first plate of a bone distraction device to a first bone segment of the subject; anchoring a second plate of the bone distraction device to a second bone segment of the subject; thereafter associating a remotely-actuated expansion system with the first plate and the second plate; remotely actuating the remote-actuated expansion system, after callus bone has formed between the first bone segment and the second bone segment, to force the first plate and the second plate apart relative to each other; thereafter allowing additional callus bone to form between the first bone segment and the second bone segment; and repeating the steps of remotely actuating the remote-actuated expansion system and thereafter allowing additional callus bone to form between the first bone segment and the second bone segment until the bone has been lengthened to a desired extent. In some embodiments, the step of remotely actuating the remote-actuated expansion system comprises remotely applying a wireless signal that causes an increase in a temperature of a shape memory alloy within the remote-actuated expansion system. In some embodiments, the step of allowing additional callus bone to form between the first bone segment and the second bone segment comprises wirelessly obtaining data from one or more sensor components of the bone distraction device. In some embodiments, the data comprises force data. In some embodiments, the data comprises vibration data. In some embodiments, the data comprises electromagnetic data. In some embodiments, the data comprises acoustic data. In some embodiments, the data comprises dielectric permittivity data. In some embodiments, the method further comprises preventing remote actuating of the remote-actuated expansion system if the data from the one or more sensor components indicates formation of callus bone to an extent below a threshold level.

CONCLUSION

The foregoing descriptions of specific embodiments of the present invention have been presented for purposes of illustration and description. They are not intended to be exhaustive or to limit the invention to the precise forms disclosed, and obviously many modifications and variations are possible in light of the above teaching. The embodiments were chosen and described in order to best explain the principles of the invention and its practical application, to thereby enable others skilled in the art to best utilize the invention and various embodiments with various modifications as are suited to the particular use contemplated. It is intended that the scope of the invention be defined by the Claims appended hereto and their equivalents.

It is to be understood that both the foregoing descriptions are exemplary and explanatory only, and are not restrictive of the methods and devices described herein. In this application, the use of the singular includes the plural unless specifically stated otherwise. Also, the use of "or" means "and/or" unless stated otherwise. Similarly, "comprise," "comprises," "comprising," "include," "includes" and "including" are not intended to be limiting.

All patents, patent applications, publications, and references cited herein are expressly incorporated by reference to the same extent as if each individual publication or patent application was specifically and individually indicated to be incorporated by reference.

What is claimed is:

1. A method of lengthening a bone in a subject, the method comprising:
    anchoring a first block portion (3) of a subcutaneous bone distraction device (1) to a first bone section of the bone (2);
    anchoring a second block portion (3') of the subcutaneous bone distraction device (1) to a second bone section of the bone (2');
    actuating a push button expansion system (5'-6-7-8-8') of the subcutaneous bone distraction device to incrementally and slidably advance the second block portion (3') along a pair of opposing rails (3a) of the first block portion (3);
    waiting a length of time;
    thereafter actuating the push button expansion system (5'-6-7-8-8') to incrementally and slidably advance the second block portion (3') along the pair of opposing rails (3a) of the first block portion (3); and
    repeating the steps of waiting a length of time and thereafter actuating the push button expansion system until the bone has been lengthened to a desired length;
    wherein the push button expansion system (5'-6-7-8-8') comprises an actuator (7) for receiving an activation force from a user, a floating element (6) for transferring input from the actuator (7) into lateral motion, a second locking pawl (5') associated with the floating element (6) and with a pair of opposing ratchet sections (4) of the first block portion (3), a first energy storage element (8) associated with the floating element (6) for returning the floating element (6) to an initial position, and a second energy storage element (8') for returning the actuator (7) to the initial position after receiving the activation force from the user.

2. The method of claim 1, wherein the pair of opposed ratchets (4) enable the incremental and sliding advancement of the second block portion (3') upon activation of the push button expansion system (5'-6-7-8-8').

3. The method of claim 1, wherein the second block portion (3') further comprises a first locking pawl (5) for engaging a pair of opposed ratchets (4).

4. The method of claim 1, wherein each activation of the push button expansion system (5'-6-7-8-8') expands the second block portion (3') along the pair of opposing rails (3a) by no more than 0.25 mm.

5. The method of claim 1, wherein each activation of the push button expansion system (5'-6-7-8-8') expands the second block portion (3') along the pair of opposing rails (3a) by no more than 0.2 mm.

6. The method of claim 1, wherein each activation of the push button expansion system (5'-6-7-8-8') expands the second block portion (3') along the pair of opposing rails (3a) by no more than 0.15 mm.

7. The method of claim 1, wherein each activation of the push button expansion system (5'-6-7-8-8') expands the second block portion (3') along the pair of opposing rails (3a) by no more than 0.1 mm.

8. The method of claim 1, further comprising performing an osteotomy on the bone to separate the first bone section (2) from the second bone section (2') before the steps of anchoring the first block portion (3) of the subcutaneous bone distraction device (1) to the first bone section (2) and anchoring the second block portion (3') of the subcutaneous bone distraction device (1) to the second bone section (2').

9. The method of claim 1, further comprising, after the bone has been lengthened to a desired length, removing the first block portion (3) from the first bone section (2) and removing the second block portion (3') from the second bone section (2').

10. The method of claim 1, further comprising determining an extent of callus growth between the first bone section (2) and the second bone section (2') after the step of actuating the push button expansion system (5'-6-7-8-8') and the step of thereafter actuating the push button expansion system (5'-6-7-8-8'), wherein the step of thereafter actuating the push button expansion system (5'-6-7-8-8') occurs only after the extent of callus growth is determined to be sufficient.

11. The method of claim 10, wherein the step of determining the extent of callus growth comprises obtaining callus stiffness information from at least one sensor in wireless communication with a data receiving device.

12. The method of claim 11, wherein the at least one sensor comprises a first sensor associated with the first locking pawl (5) and a second sensor (9') associated with the second locking pawl (5').

13. The method of claim 11, wherein the at least one sensor comprises a force sensor (10) associated with the first locking pawl (5).

14. The method of claim 11, wherein the at least one sensor comprises a bone regeneration sensor (11) associated with the first block portion (3) or with the second block portion (3') for determining the callus stiffness.

15. The method of claim 14, wherein the bone regeneration sensor (11) is a vibration sensor.

16. The method of claim 14, wherein the bone regeneration sensor (11) is an acoustic emission sensor.

17. The method of claim 14, wherein the bone regeneration sensor (11) is a dielectric sensor.

18. The method of claim 11, wherein the at least one sensor comprises a plurality of bone regeneration sensors (12) associated with the first block portion (3) or with the second block portion (3').

19. The method of claim 18, wherein the plurality of bone regeneration sensors (12) is positioned along a length of the first block portion (3) or along a length of the second block portion (3').

* * * * *